US012642539B2

(12) United States Patent
Gerges et al.

(10) Patent No.: US 12,642,539 B2
(45) Date of Patent: Jun. 2, 2026

(54) HIP BROACH AND IMPLANT DESIGNED USING MORPHOLOGICAL DATA

(71) Applicant: Howmedica Osteonics Corp., Mahwah, NJ (US)

(72) Inventors: Justin Joseph Gerges, Teaneck, NJ (US); Sonia Donde, Jersey City, NJ (US); Joshua Peterson, Warwick, NY (US); Matthew Demers, Ramsey, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 540 days.

(21) Appl. No.: 17/989,955

(22) Filed: Nov. 18, 2022

(65) Prior Publication Data

US 2023/0157709 A1      May 25, 2023

Related U.S. Application Data

(60) Provisional application No. 63/282,286, filed on Nov. 23, 2021.

(51) Int. Cl.
    *A61B 17/16*          (2006.01)
(52) U.S. Cl.
    CPC ................................ *A61B 17/1668* (2013.01)
(58) Field of Classification Search
    CPC ............ A61B 17/1659; A61B 17/1664; A61B 17/1668
    See application file for complete search history.

(56) References Cited

U.S. PATENT DOCUMENTS

| | | | |
|---|---|---|---|
| 3,815,599 | A | 6/1974 | Deyerle |
| 4,406,023 | A | 9/1983 | Harris |
| D272,648 | S | 2/1984 | Bolesky et al. |
| 4,514,865 | A | 5/1985 | Harris |
| 4,530,116 | A | 7/1985 | Frey |
| 4,535,487 | A | 8/1985 | Esper et al. |
| 4,546,501 | A | 10/1985 | Gustilo et al. |

(Continued)

FOREIGN PATENT DOCUMENTS

| | | |
|---|---|---|
| CN | 305511464 | 12/2019 |
| FR | 2851456 A1 | 8/2004 |
| FR | 2961684 A1 | 12/2011 |
| WO | 2018183168 A1 | 10/2018 |
| WO | 2023027952 A1 | 3/2023 |

OTHER PUBLICATIONS

Wuestemann T, Bastian A, Parvizi J, et al. A novel tapered hip stem design optimized for femoral fit in a wide array of bone types. EFORT. Jul. 1-4, 2011; Copenhagen. Free Paper Session 2478, copyright 2011, Stryker Co., 15 slides.

(Continued)

*Primary Examiner* — Si Ming Ku
(74) *Attorney, Agent, or Firm* — Lerner David LLP

(57) ABSTRACT

In one embodiment, the present disclosure relates to a broach for use in a mammalian femur. The broach includes a body with a proximal portion and a distal portion extending from the proximal portion. The proximal portion has a first surface with a plurality of first teeth and the distal portion has a second surface with a plurality of second teeth. Each of the second teeth is different from each of the first teeth. And, each of the plurality of second teeth include pointed protrusions extending outward from the second surface.

20 Claims, 13 Drawing Sheets

(56) References Cited

U.S. PATENT DOCUMENTS

| | | | |
|---|---|---|---|
| 4,549,319 A | 10/1985 | Meyer | |
| 4,552,136 A | 11/1985 | Kenna | |
| D283,731 S | 5/1986 | Kenna | |
| D284,100 S | 6/1986 | Kenna | |
| 4,608,053 A * | 8/1986 | Keller | A61F 2/30728 |
| | | | 623/23.31 |
| 4,612,160 A | 9/1986 | Donlevy et al. | |
| 4,713,076 A | 12/1987 | Draenert et al. | |
| 4,718,912 A | 1/1988 | Crowninshield | |
| 4,795,472 A | 1/1989 | Crowninshield et al. | |
| 4,840,632 A | 6/1989 | Kampner | |
| 4,917,702 A | 4/1990 | Scheicher et al. | |
| 4,919,665 A | 4/1990 | Homsy | |
| 4,983,183 A | 1/1991 | Horowitz | |
| 5,002,580 A | 3/1991 | Noble et al. | |
| 5,004,476 A | 4/1991 | Cook | |
| 5,007,931 A | 4/1991 | Smith | |
| 5,041,118 A | 8/1991 | Wasilewski | |
| 5,047,054 A | 9/1991 | Vijayan et al. | |
| 5,080,673 A | 1/1992 | Burkhead et al. | |
| 5,089,004 A | 2/1992 | Averill et al. | |
| 5,133,771 A | 7/1992 | Duncan et al. | |
| 5,147,408 A | 9/1992 | Noble et al. | |
| 5,163,961 A | 11/1992 | Harwin | |
| 5,176,712 A | 1/1993 | Homsy | |
| 5,258,035 A | 11/1993 | Hofmann et al. | |
| 5,314,489 A | 5/1994 | Hoffman et al. | |
| 5,336,265 A | 8/1994 | Serbousek et al. | |
| D364,926 S | 12/1995 | Webb, Jr. et al. | |
| 5,514,184 A | 5/1996 | Doi et al. | |
| 5,607,607 A | 3/1997 | Naiman et al. | |
| 5,665,091 A * | 9/1997 | Noble | A61B 17/1659 |
| | | | 606/85 |
| 5,681,315 A | 10/1997 | Szabo | |
| 5,766,261 A | 6/1998 | Neal et al. | |
| 5,807,407 A | 9/1998 | England et al. | |
| 5,810,830 A | 9/1998 | Noble et al. | |
| 5,814,049 A | 9/1998 | Pratt et al. | |
| 5,879,401 A | 3/1999 | Besemer et al. | |
| 6,045,556 A | 4/2000 | Cohen | |
| 6,058,590 A | 5/2000 | Roberts et al. | |
| 6,193,759 B1 | 2/2001 | Ro et al. | |
| 6,652,591 B2 | 11/2003 | Serbousek et al. | |
| 6,656,187 B1 | 12/2003 | Camino | |
| 6,663,636 B1 | 12/2003 | Lin | |
| 6,695,884 B1 | 2/2004 | Townley | |
| 6,749,639 B2 | 6/2004 | Lewallen | |
| 6,875,092 B2 | 4/2005 | Brookins et al. | |
| 6,926,741 B2 | 8/2005 | Kolb | |
| 6,949,124 B2 | 9/2005 | Serbousek et al. | |
| 6,974,482 B2 | 12/2005 | Zhu | |
| 7,179,264 B2 | 2/2007 | Cassell | |
| 7,214,246 B2 | 5/2007 | Serbousek et al. | |
| 7,273,499 B2 | 9/2007 | McCleary et al. | |
| 7,481,842 B2 | 1/2009 | Noetzli et al. | |
| 7,494,509 B1 | 2/2009 | Hershberger et al. | |
| 7,537,664 B2 | 5/2009 | O'Neill et al. | |
| 7,828,851 B2 | 11/2010 | McCleary et al. | |
| 7,842,096 B2 | 11/2010 | Fridshtand et al. | |
| 7,947,084 B2 | 5/2011 | Link | |
| 7,976,545 B2 | 7/2011 | Hershberger et al. | |
| 7,976,548 B2 | 7/2011 | Burgi et al. | |
| 8,454,611 B2 | 6/2013 | Wallstein et al. | |
| 8,529,569 B2 | 9/2013 | Smith et al. | |
| 8,562,609 B2 | 10/2013 | Schnieders et al. | |
| 8,562,690 B1 | 10/2013 | Dickerson | |
| 8,641,772 B2 | 2/2014 | Link | |
| 8,657,834 B2 | 2/2014 | Burgi | |
| 8,679,127 B2 | 3/2014 | Biegun et al. | |
| 8,728,387 B2 | 5/2014 | Jones et al. | |
| 8,870,875 B2 | 10/2014 | Romagnoli et al. | |
| 8,936,649 B2 | 1/2015 | Huff | |
| 9,023,419 B2 | 5/2015 | Meehan et al. | |
| 9,034,051 B2 | 5/2015 | Kokubo et al. | |
| 9,089,441 B2 | 7/2015 | Reignier et al. | |
| 9,180,010 B2 | 11/2015 | Dong et al. | |
| 9,216,929 B2 | 12/2015 | Andersch et al. | |
| 9,301,765 B2 | 4/2016 | Chow et al. | |
| D757,269 S | 5/2016 | Prybyla et al. | |
| 9,375,324 B2 | 6/2016 | Reignier et al. | |
| 9,492,184 B2 | 11/2016 | Kurtz | |
| 9,662,122 B2 | 5/2017 | Young | |
| 9,750,850 B2 | 9/2017 | Fonte et al. | |
| 9,775,628 B2 | 10/2017 | Monaghan | |
| 9,844,438 B2 | 12/2017 | McHugh et al. | |
| 9,861,374 B2 | 1/2018 | Reu et al. | |
| 9,937,048 B2 | 4/2018 | Grostefon et al. | |
| 10,070,962 B1 | 9/2018 | Moore et al. | |
| 10,098,745 B1 | 10/2018 | Lyren | |
| 10,188,405 B2 | 1/2019 | Duncan et al. | |
| 10,238,402 B2 | 3/2019 | Macke et al. | |
| 10,251,752 B2 | 4/2019 | Satterthwaite et al. | |
| 10,278,823 B1 | 5/2019 | Xue et al. | |
| 10,456,148 B2 | 10/2019 | Young | |
| 10,470,885 B2 | 11/2019 | Bake et al. | |
| 10,524,933 B2 | 1/2020 | Moore et al. | |
| 10,695,076 B2 | 6/2020 | Agunloye et al. | |
| D1,039,157 S | 8/2024 | Lima et al. | |
| D1,046,152 S | 10/2024 | Atkin et al. | |
| 12,208,024 B2 | 1/2025 | Ait Si Selmi et al. | |
| 12,295,851 B2 | 5/2025 | Armacost et al. | |
| 12,329,425 B2 | 6/2025 | Trauner et al. | |
| D1,083,099 S | 7/2025 | Russell et al. | |
| 2001/0039454 A1 | 11/2001 | Ricci et al. | |
| 2004/0249384 A1 | 12/2004 | Blaha et al. | |
| 2005/0159821 A1 | 7/2005 | Thompson et al. | |
| 2007/0233127 A1 | 10/2007 | Tuke et al. | |
| 2009/0105842 A1 | 4/2009 | Noetzli et al. | |
| 2010/0023014 A1 | 1/2010 | Romagnoli et al. | |
| 2011/0071633 A1 | 3/2011 | Fonte | |
| 2011/0251697 A1 | 10/2011 | Chung et al. | |
| 2012/0165951 A1 | 6/2012 | Forsell | |
| 2012/0265319 A1 | 10/2012 | Prybyla et al. | |
| 2014/0081274 A1 * | 3/2014 | Huff | A61B 17/1659 |
| | | | 606/85 |
| 2014/0343685 A1 | 11/2014 | Ranawat et al. | |
| 2018/0000598 A1 | 1/2018 | Amis et al. | |
| 2018/0014940 A1 | 1/2018 | Kurtz | |
| 2018/0028196 A1 | 2/2018 | Sharkey et al. | |
| 2018/0132866 A1 | 5/2018 | Muller | |
| 2018/0214275 A1 | 8/2018 | Grostefon et al. | |
| 2018/0228616 A1 | 8/2018 | Piecuch | |
| 2018/0243099 A1 | 8/2018 | Sidebotham | |
| 2018/0280036 A1 | 10/2018 | Agunloye et al. | |
| 2018/0303495 A1 | 10/2018 | Hirt et al. | |
| 2018/0333264 A1 | 11/2018 | Dressler et al. | |
| 2019/0046322 A1 | 2/2019 | Moore et al. | |
| 2019/0099191 A1 | 4/2019 | Huff et al. | |
| 2019/0151100 A1 | 5/2019 | Armacost et al. | |
| 2019/0247061 A1 | 8/2019 | Huff et al. | |
| 2019/0247063 A1 | 8/2019 | Huff et al. | |
| 2019/0336145 A1 | 11/2019 | Bader et al. | |
| 2020/0222208 A1 | 7/2020 | Bushell et al. | |
| 2020/0276029 A1 | 9/2020 | Bailey | |
| 2021/0093459 A1 | 4/2021 | Satterthwaite et al. | |
| 2021/0093460 A1 | 4/2021 | Satterthwaite et al. | |
| 2021/0237149 A1 | 8/2021 | Julien et al. | |
| 2023/0157709 A1 | 5/2023 | Gerges et al. | |
| 2024/0197483 A1 | 6/2024 | Gugler et al. | |
| 2024/0206888 A1 | 6/2024 | Karas | |
| 2024/0341977 A1 | 10/2024 | Rister et al. | |
| 2024/0366390 A1 | 11/2024 | de Beaubien et al. | |
| 2025/0041075 A1 | 2/2025 | Rister et al. | |
| 2025/0114203 A1 | 4/2025 | Hunt et al. | |

OTHER PUBLICATIONS

Kolisek, F. et al., "Mid-Term Follow Up of Newer-Generation Morphometric Wedge Stems for Total Hip Arthroplasty (THA)". Orthopaedic Surgery, Surgical Technology International. May 28, 2020; 36:399-403. PMID: 32243564.5 pgs.

(56) References Cited

OTHER PUBLICATIONS

Pierce T. et al., "Second-Generation Versus First-Generation Cementless Tapered Wedge Femoral Stems". Orthopedics. Sep. 2015 38(9): pp. 550-554.

Narzikul, BS. et al., "Alteration in Geometry of Femoral Stem Results in Better Fit and Fill: Comparison of Accolade I vs. Accolade II". Presentation at 47th Annual EOA Meeting-New Orleans, LA, Oct. 19-22, 2016. 1 pg.

Khanuja H, et al., "Current Concepts Review: Cementless Femoral Fixation in Total Hip Arthroplasty". J Bone Joint Surg Am. 2011;93: pp. 500-509.

Lawrie, C.M., et al., "Modular dual mobility total hip arthroplasty is a viable option for young, active patients". Bone and Joint Journal. Jul. 2021; I 03-B(7 Supple B): pp. 73-77.

Johnson, A. et al., "A Calcar Collar Is Protective Against Early Torsional/Spiral Periprosthetic Femoral Fracture: A Paired Cadaveric Biomechanical Analysis". Journal of Bone Joint Surgery. Aug. 2020; 102: pp. 1427-1433; http://dx.doi.org/10.2106/JBJS.19.01125.

Demey, G. et al., "Does a Collar Improve the Immediate Stability of Uncemented Femoral Hip Stems in Total Hip Arthroplasty?" A Bilateral Comparative Cadaver Study. The Journal of Arthroplasty. vol. 26 No. 8 Dec. 2011, pp. 1549-1555.

Lamb, J. et al., "Calcar-collar contact during simulated periprosthetic femoral fractures increases resistance to fracture and depends on the initial separation on implantation: A composite femur in vitro study." Clinical Biomechanics. 87 Jul. 2001, 105411. https://doi.org/10.1016/j.clinbiomech.2021.105411. 6 pgs.

Qiu, J. et al., "Risk factors for iliopsoas impingement after total hip arthroplasty using a collared femoral prosthesis." Journal of Orthopaedic Surgery and Research, Jul. 2020, 15:267. https://doi.org/10.1186/s13018.-020-01787-3. 8 pgs.

Macfarlane, R J., et al., "Trochanteric Bursitis In Association With high Offset Femoral Stem Components In Total Hip Arthroplasty". Orthopaedic Proceedings vol. 92-B, No. Supp III. (Feb. 2018). 2 pgs.

Imami, D. et al., "Comparison of femoral hip stem seating heights in two femoral broach designs". ORS Abstract 2021. Feb. 2022. 1 pg.

Brzezinski, Andrzej et al., "A Unique Complication of Femoral Broach Fracture and Incarceration During Total Hip Arthroplasty." Arthroplasty today vol. 11, pp. 49-53. Aug. 21, 2021, doi:10.1016/j.artd.2021.07.011.

American Joint Replacement Registry, 2020 Supplemental Report. Obtained in table 1.1 in 2020 AJRR Supplemental Report. Aug. 2021. 2 pgs.

Heffernan C, Bhimji S, Macintyre S, et al. Development and. validation of a novel modular dual mobility hip bearing. Presented at: Orthopaedic Research Society (ORS) Annual Meeting; Jan. 13-16, 2011; Long Beach, CA. 1 pg.

Epinette JA, Harwin SF, Rowan FE, et al. Early experience with dual mobility acetabular systems featuring highly cross-linked polyethylene liners for primary hip arthroplasty in patients under fifty five years of age: an international multi-centre preliminary study. International Orthopaedics. Mar. 2017;41(3):543-550. doi:10.1007/s00264-016-3367-06. 8 pgs.

Jauregui JJ, Pierce TP, Elmallah RK, Cherian JJ, Delanois RE, Mont MA. Dual mobility cups: an effective prosthesis in revision total hip arthroplasties for preventing dislocations. Hip International. Jan.-Feb. 2016;26(1): pp. 57-61. doi:10.5301/hipint.50002957.

Mont MA, Issa K, Naziri Q, Harwin SF, Delanois RE, Johnson AJ. The Use of Dual-Mobility Bearings in Difficult Hip Arthroplasty Reconstructive Cases. Surgical Technology International. Dec. 2011;21:pp. 234-240.

Hartzler MA, et al., Otto Aufranc Award: Dual-mobility Constructs in Revision THA Reduced Dislocation, Rerevision, and Reoperation Compared With Large Femoral Heads. Clin Orthop Relat Res. Feb. 2018;476(2): pp. 293-301. doi:10.1007/s11999.00000000000000359.

Herrera L, Longaray J, Essner A. Edge loading wear due to inclination angle for three contemporary hip bearings. Presented at: Orthopaedic Research Society (ORS) Annual Meeting; Mar. 6-9, 2010; New Orleans, LA. 1 pg.

Wang A, Essner A, Polineni VK, Stark C, Dumbleton JH. Lubrication and wear of ultra-high molecular weight polyethylene in total joint replacements. Tribology International. Jan. 1998;31(1-3): pp. 17-33. doi:10.1016/S0301-679X(98)00005-X.

Essner A, Polineni VK, Wang A, Stark C, Dumbleton JH. Hip simulator wear of "enhanced" UHMWPE acetabular inserts. Presented at: Orthopaedic Research Society (ORS) 44th Annual Meeting; Mar. 16-19, 1998; New Orleans, A. 1 pg.

Essner A, Wang A, Martell J, Edidin A. In-vitro and in-vivo acetabular cup wear corroboration. Presented at: Orthopaedic Research Society (ORS) 47th Annual Meeting; Feb. 25-28, 2001; San Francisco, CA. 1 pg.

Australian Orthopedic Association National Joint Replacement Registry, 2021 Annual Report. 5-year and 20-year revision rate obtained from table HT12 in AOANJRR 2021 Annual Report, Sep. 1999-Dec. 2000. <https://aoanjrr.sahmri.com/annual-reports-2021>. 1-216 out of 436 pgs. (Part 1 of 2).

Australian Orthopedic Association National Joint Replacement Registry, 2021 Annual Report. 5-year and 20-year revision rate obtained from table HT12 in AOANJRR 2021 Annual Report, Sep. 1999-Dec. 2000. <https://aoanjrr.sahmri.com/annual-reports-2021>. 217-434 out of 436 pgs. (Part 2 of 2).

Extended European Search Report issued in Appln. No. 22209055.7 mailed Mar. 24, 2023 (3 pages).

* cited by examiner

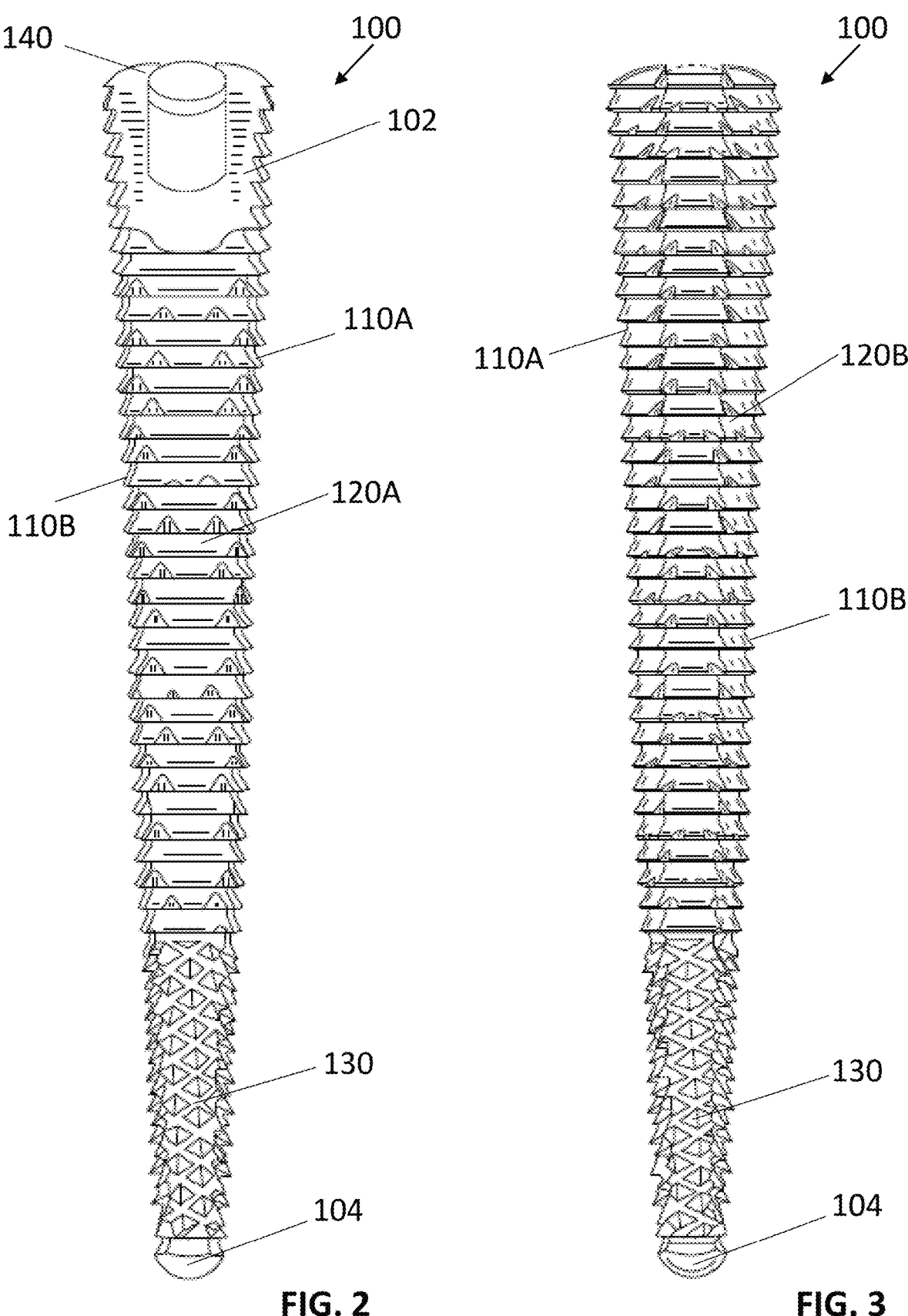
FIG. 2          FIG. 3

SECTION AA-AA

SECTION BB-BB

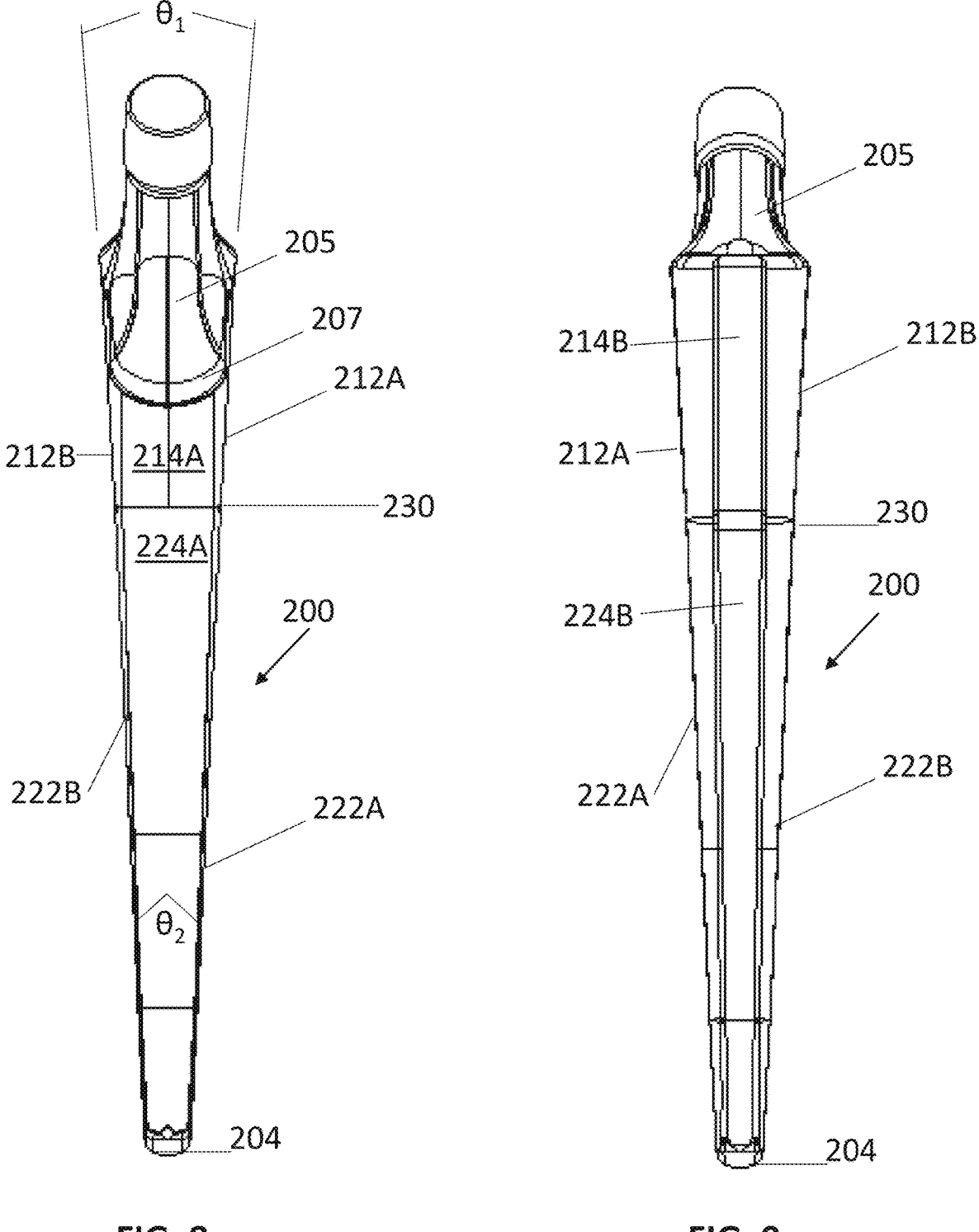
FIG. 8                      FIG. 9

10

Femoral Head Center

Greater trochanter

70
Femur Central Axis

Lesser trochanter

Posterior Point — 80A
Lateral Point — 80B
— 80C
— 80D
— 80E
— 80F
— 80G
— 80H
— 80I
— 80J
— 80K
— 80L
— 80M
— 80N Medial Point Anterior Point

14

80A

Posterior 81A

70

Medial
83A

Center
Axis

Lateral
84A

Anterior 82A

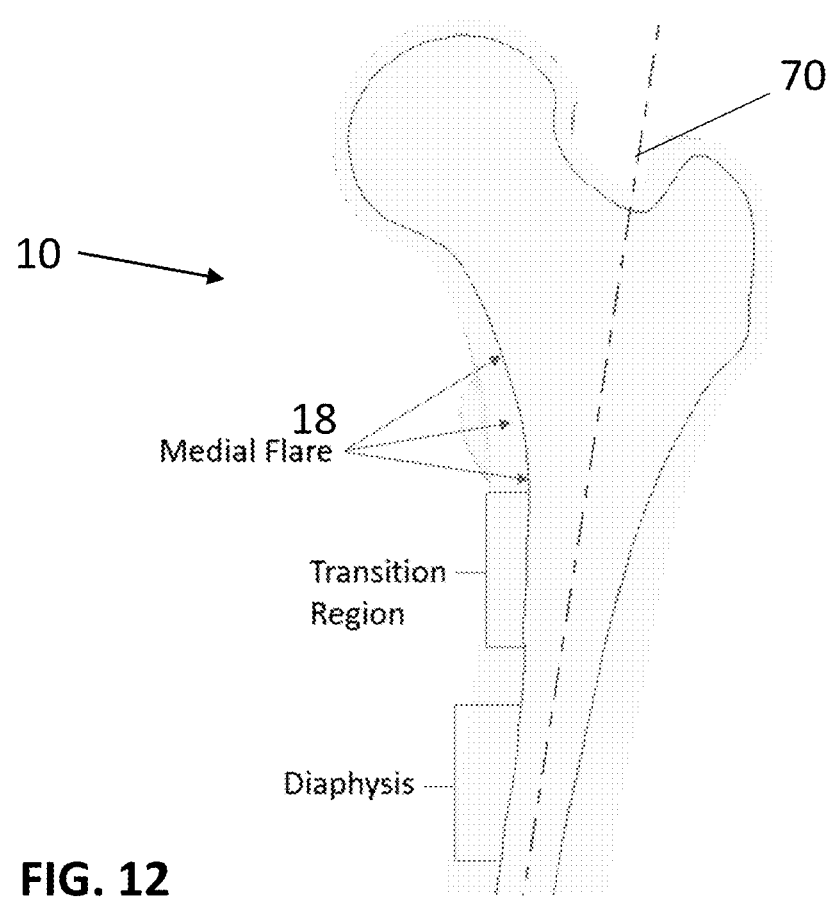
FIG. 12
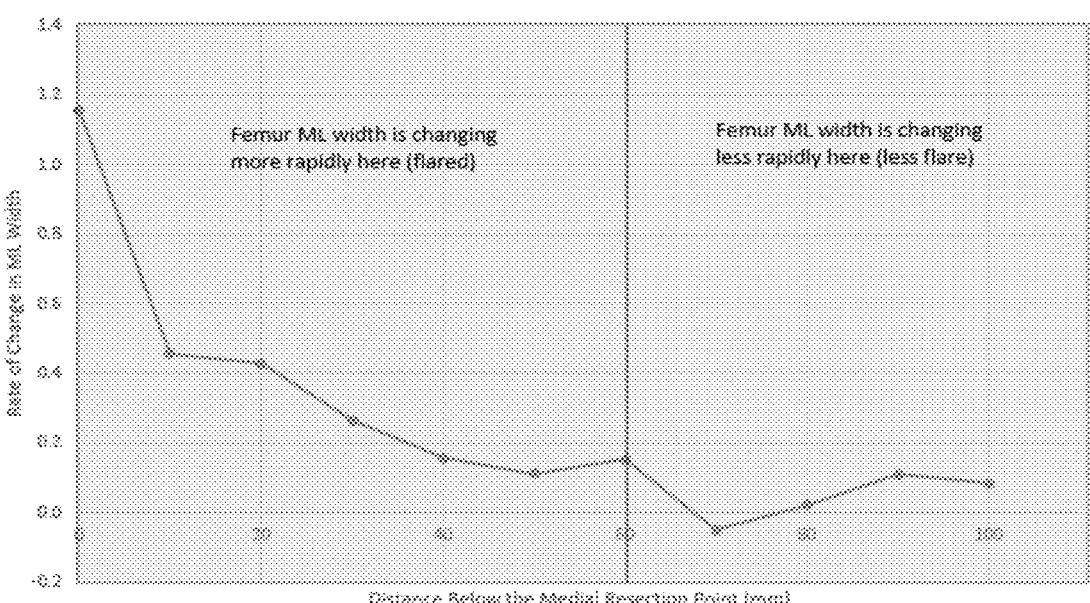
FIG. 13

310

Simulated Neck Resection Plane

336

334
Endocortical Resection Point

Periosteal Resection Point 332

310

370

Medial-Lateral width from center axis

372

207

Periosteal Boundary

373

230

200

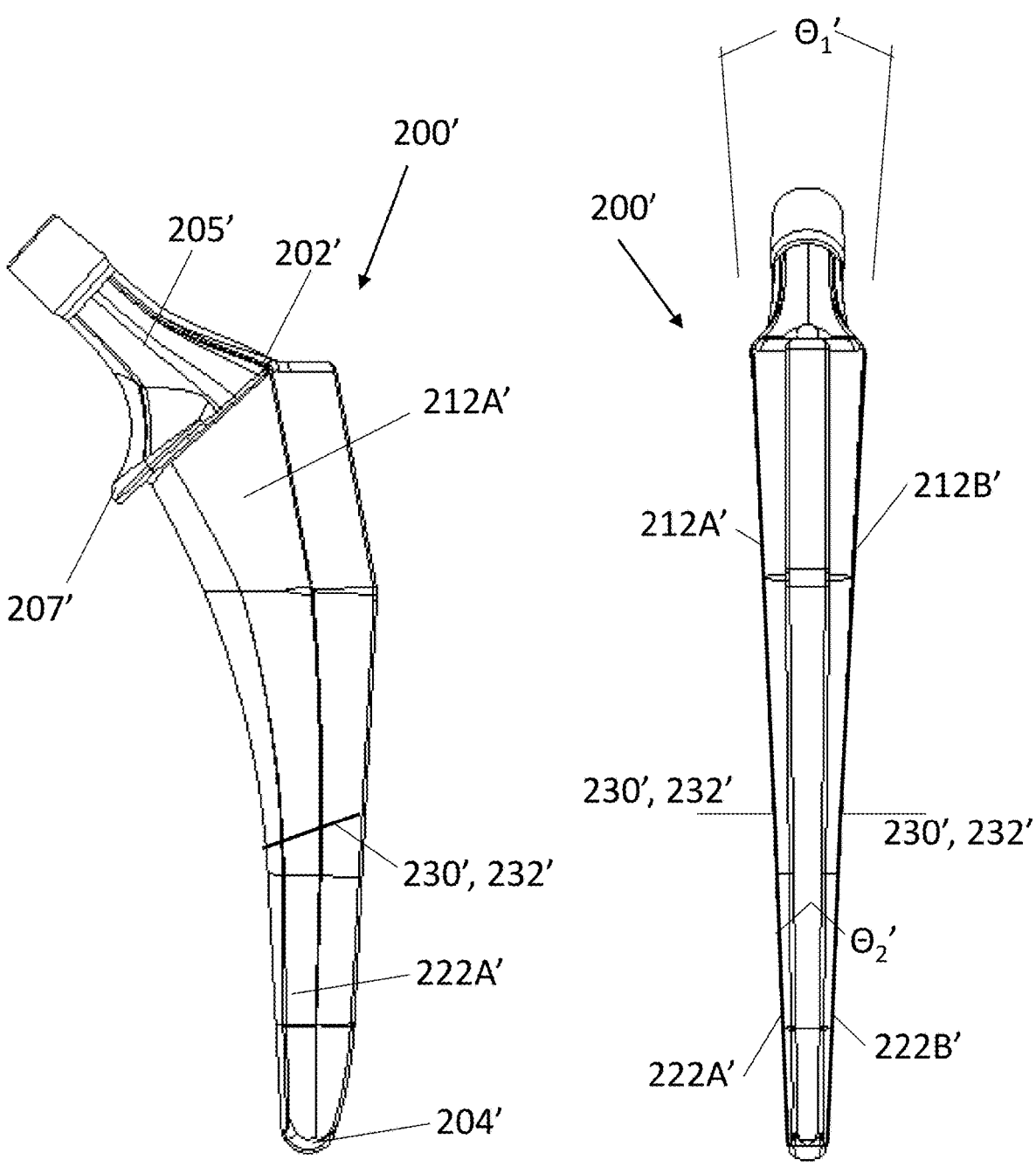
FIG. 21                    FIG. 22

HIP BROACH AND IMPLANT DESIGNED USING MORPHOLOGICAL DATA

CROSS-REFERENCE TO RELATED APPLICATION

The present application claims the benefit of the filing date of U.S. Provisional Patent Application No. 63/282,286, filed Nov. 23, 2021, the disclosure of which is hereby incorporated by reference herein in its entirety.

BACKGROUND OF THE DISCLOSURE

When a patient suffers a condition in the hip joint such as joint disease resulting from osteoarthritis, rheumatoid arthritis or post-traumatic arthritis, functional deformities, fractures in a proximal part of the femur, or a poorly performing implant from a previous procedure, such conditions may be treated through a hip joint replacement procedure.

During replacement surgeries, a broach is typically used to prepare a femoral canal to receive a femoral hip implant, and the hip implant is later disposed in the prepared canal. One challenge with existing broach technologies is their limited capacity to remove cortical bone in more distal regions that would receive a distal part of a hip implant. This is particularly the case when a patient is younger, as such patients may have femurs that have narrower cross-sections in the diaphysis. Under such circumstances, it may be more difficult to reach such distal regions of the femur with existing broaches and reaming tools. Insufficient broaching in the diaphysis may lead to undesirable engagement of the hip implant in that region, reducing the likelihood of a successful procedure.

Existing hip implant designs and methods of their implantation, particularly those intended for cementless fixation, often suffer from inefficiencies due to difficulty in obtaining a desired level of fixation between the implant and the cortical bone of the femur. For instance, existing designs exhibit limitations in controlling where fixation between the implant and the bone will occur.

Accordingly, there is a need for improvements in broach and femoral hip implant designs that will further enhance surgical outcomes that result from a hip joint replacement.

BRIEF SUMMARY OF THE DISCLOSURE

The present disclosure provides improvements in hip implant procedures and hip implants themselves. A broach is contemplated that includes a proximal region and a distal region. Both regions, throughout a body of the stem, include cutting teeth. In the distal region, the teeth are more aggressive than in the proximal region. In some examples, the teeth in the distal region are diamond-shaped while the teeth in the proximal region have elongate ridges between troughs. This design minimizes excess removal of bone material in a metaphysis of a femur while promoting removal of material in a diaphysis region of the femur, where clearance between an implant surface and the cortical bone is desired.

The present disclosure also contemplates a hip implant in the form of a stem sized for implantation in a femur. The hip implant has a shape that optimizes engagement of medial and lateral sides of the implant with cortical bone in the metaphysis region of the femur while minimizing engagement of the implant with cortical bone in the diaphysis region.

In one aspect, the present disclosure relates to a broach for use in a mammalian femur. In a first example of a first embodiment of the broach, the broach includes a body with a proximal portion and a distal portion extending from the proximal portion. The proximal portion has a first surface with a plurality of first teeth and the distal portion has a second surface with a plurality of second teeth. At least one tooth of the plurality of second teeth is different from at least one tooth of the plurality of first teeth and at least one tooth of the plurality of second teeth may include a pointed protrusion that extends outward from the second surface. In some variations of the first example, at least one tooth of the plurality of second teeth is different from each of the plurality of first teeth. In other variations of the first example, each tooth of the plurality of second teeth is different from at least one tooth of the plurality of first teeth. In further variations, each tooth of the plurality of second teeth is different from each tooth of the plurality of first teeth.

In a second example, the first example of the first embodiment may be further defined by the pointed protrusion of the at least one tooth of the plurality of second teeth having a leading surface that is oriented at a steeper angle than a flank trailing the pointed protrusion. In a third example, the first example of the first embodiment may be further defined by the plurality of second teeth extending around an entire perimeter of the distal portion. In a fourth example, any one of the first through third examples of the first embodiment may be further defined by each of the plurality of first teeth including an elongate sharp ridge surrounded on all sides by troughs separating each elongate sharp ridge. In a fifth example, the fourth example of the first embodiment may be further defined by the proximal portion having a third surface with a plurality of third teeth different from the plurality of first teeth. In some variations, the third surface does not overlap the first surface and each of the first surface and the third surface extend along a length of the proximal portion.

In a sixth example, any one of the first through fifth examples of the first embodiment may be further defined by at least some of the plurality of second teeth being located less than 25% of a distance from a distal tip of the body to a proximal end of the body. In a seventh example, the sixth example of the first embodiment may be further defined by the distal portion being located entirely within 40% of a distance from the distal tip of the body to the proximal end of the body. In an eighth example, the seventh example of the first embodiment may be further defined by the plurality of second teeth extending over a majority of the second surface. Further, the second surface may be coincident with the distal portion. In a ninth example, the eighth example of the first embodiment may be defined by the plurality of second teeth being only in the distal portion. In a tenth example, any one of the first through ninth examples of the first embodiment may include a transition between the proximal portion and the distal portion that is in a range of 60 mm to 80 mm from a medial proximal end located in the proximal portion. In an eleventh example, the fourth example of the first embodiment may be further defined by the proximal portion including a third surface with a plurality of third teeth having flat protruding ridges. In a twelfth example, the eleventh example of the first embodiment may be defined by the first surface of the proximal portion including a medial surface and a lateral surface and the third surface including an anterior surface and a posterior surface.

The first embodiment may be varied in other ways as described through the following additional examples. In a thirteenth example, the broach of the first example may include the plurality of second teeth having pointed protrusions with leading surfaces oriented at a steeper angle than flanks trailing the pointed protrusions. In a fourteenth example, the plurality of first teeth in the broach of any one of the first and thirteenth examples may include elongate sharp ridges surrounded on all sides by troughs separating each elongate sharp ridge. In a fifteenth example, the broach of any one of the first, thirteenth and fourteenth examples may include a third surface with a plurality of third teeth different from the plurality of first teeth, the third surface not overlapping the first surface and each of the first surface and the third surface extending along a length of the proximal portion. In a sixteenth example, the proximal portion in the broach of the fifteenth example may include a third surface with a plurality of third teeth having elongate flat protruding ridges. In a seventeenth example, the body of the broach of any one of the fifteenth and sixteenth examples may include a medial surface, a lateral surface, an anterior surface and a posterior surface. The first surface may be solely on the medial and lateral surfaces in the proximal portion and the third surface may be solely on the anterior and posterior surfaces in the proximal portion such that third teeth are absent from the medial and lateral surfaces and first teeth are absent from anterior and posterior surfaces. In some examples, the first teeth may be disposed on a majority of the medial and lateral surfaces in the proximal portion. In other examples, the first teeth may be disposed on an entirety of the medial and lateral surfaces of the proximal portion. In some examples, the third teeth may be on a majority of the anterior and posterior surfaces in the proximal portion. In other examples, the third teeth may be on an entirety of the anterior and posterior surfaces in the proximal portion. In an eighteenth example, the plurality of second teeth in the broach of the seventeenth example may be disposed on the medial, lateral, anterior and posterior surfaces within the distal portion.

In a nineteenth example, the distal portion of the broach of any one of the first and thirteenth through eighteenth examples may be located entirely within 40% of a distance from a distal tip of the body at a distal end of the distal portion to a proximal end of the body at a proximal end of the proximal portion. In some examples, the distal portion may be located entirely within 50% of a distance from the distal tip of the body to the proximal end of the body. In some examples, the distal portion may be located entirely within 30% of the distance from the distal tip of the body to the proximal end of the body. In still further examples, the extent of the distal portion may be any value in a range from 30% to 50% of the distance from the distal tip to the proximal end. In still further examples, the extent of the distal portion may be outside of this range. Such circumstances may arise as a function of patient anatomy.

In a twentieth example, the broach of any one of the first and thirteenth through nineteenth examples may include at least some of the plurality of second teeth within 10% of the distance from the distal tip of the body to the proximal end of the body. In other examples, the plurality of second teeth may be disposed distally up to within 5% of the distance from the distal tip to the proximal end. In further examples, a distal extent of the second teeth of the plurality of second teeth may be even closer to the distal tip than 5% of the distance from the distal tip, or any amount from 5% to 10% of the distance. While it is possible to vary the extent of the disposal of the second teeth, many embodiments include disposal throughout a significant surface area of the distal portion to maximize cutting performance.

In a twenty-first example, the plurality of second teeth of the broach of any one of the first and thirteenth through twentieth examples may extend over a majority of the second surface and the second surface is coincident with an entirety of an outer surface of the distal portion. In a twenty-second example, the plurality of second teeth of the broach in any one of the first and thirteenth through twenty-first examples may be solely in the distal portion. In a twenty-third example, the proximal portion of the broach of any one of the first and thirteenth through twenty-second examples may include a medial proximal end and a transition between the proximal portion and the distal portion is in a range of 60 mm to 80 mm from the medial proximal end. In a twenty-fourth example, the broach of any one of the first and thirteenth through twenty-third examples may include teeth that define linear troughs. The plurality of first teeth may define a first plurality of linear troughs and the plurality of second teeth may define a second plurality of linear troughs. Each one of the first plurality of linear troughs may be parallel to the others and each one of the second plurality of linear troughs may be parallel to the others. The second plurality of linear troughs may be transverse to the first plurality of linear troughs. In a twenty-fifth example, the plurality of second teeth of the broach of the twenty-fourth example may define a third plurality of linear troughs, each of the third plurality of linear troughs being transverse to each of the first plurality of linear troughs and the second plurality of linear troughs. In some examples, the first plurality of linear troughs may be perpendicular to an elongate dimension of the body. In a twenty-sixth example, the body of the broach of any one of the first and thirteenth through twenty-fifth examples may include a transition region defined by a distal end region of the proximal portion and a proximal end region of the distal portion, the plurality of first teeth transitioning to the plurality of second teeth in the transition region.

In a first example of a second embodiment of the broach, a broach for use in a mammalian femur includes a body with a proximal portion and a distal portion separated from the proximal portion by a transition region. The proximal portion has a first toothed surface extending over a first distance along a length of the body and the distal portion has a second toothed surface extending over a second distance along the length of the body. The distances are dimensioned such that the first distance is greater than the second distance. The first toothed surface has a plurality of first cutting surfaces and the second toothed surface has a plurality of second cutting surface. A first protruding end of at least one cutting surface of the plurality of first cutting surfaces may be longer than a second protruding end of at least one cutting surface of the plurality of second cutting surfaces. In variations of the first example, at least one cutting surface of the plurality of first cutting surfaces may be longer than each cutting surface of the plurality of second cutting surfaces. In other variations of the first example, each cutting surface of the plurality of first cutting surfaces may be longer than at least one cutting surface of the plurality of second cutting surfaces. In still further variations of the first example, each cutting surface of the plurality of first cutting surfaces may be longer than each cutting surface of the plurality of second cutting surfaces.

In a second example of the second embodiment, the first example may be defined such that the first protruding end of the at least one cutting surface of the plurality of first cutting surfaces is an elongate ridge and the second protruding end of the at least one cutting surface of the plurality of second cutting surfaces is a sharp point. In a third example of the second embodiment, the first or second example may be defined by the first distance being in a range from 50% to 70% of a combined first and second distance. In a fourth example, any one of the first through third examples of the second embodiment may be defined such that when the broach is fully disposed in a femoral canal of the mammalian femur, the transition region is aligned with a location on the femur where a medial to lateral width of the femur changes by an amount in a range of 0.25 mm per 10 mm length to 0.35 mm per 10 mm length. In a fifth example, any one of the first through third examples of the second embodiment may be further defined such that when the broach is fully disposed in a femoral canal of the mammalian femur, the transition region is aligned with a location on the femur where a first dimension from an anterior limit of the femur to a posterior limit of the femur is between 1.0 and 1.2 times a second dimension from a medial limit of the femur to lateral limit of the femur.

In a third embodiment, the present disclosure relates to a broach for use in preparing a femur to receive an implant. In one example, the broach includes a proximal portion extending along a first portion of a length of the broach and a distal portion extending along a second portion of the length of the broach, the distal portion abutting the proximal portion. The broach may be configured such that when the broach is advanced into a femur, a distal tip of the distal portion is a leading end of the broach and a proximal end of the proximal portion is a trailing end of the broach. The proximal portion may include a plurality of first cutting surfaces. The plurality of first cutting surfaces may define a first plurality of linear troughs on a surface of the proximal portion, each one of the plurality of linear troughs being parallel to the others. The distal portion may include a plurality of second cutting surfaces, the plurality of second cutting surfaces defining a second plurality of linear troughs and a third plurality of linear troughs on a surface of the distal portion. The second plurality of linear troughs may be transverse to the first plurality of linear troughs. And, the troughs may be oriented such that the third plurality of linear troughs are transverse to both the first and second plurality of linear troughs.

In a second example of the third embodiment, the broach of the first example may have second cutting surfaces such that one or more of the second cutting surfaces of the plurality of second cutting surfaces include pointed tips. One or more of the pointed tips may be an outermost projection of a surface of the broach in the distal portion. In a third example of the third embodiment, the broach of any one of the first and second examples may have a plurality of third cutting surfaces on the proximal portion. The third cutting surfaces of the plurality of third cutting surfaces may be different from the plurality of first cutting surfaces and the plurality of second cutting surfaces.

In another aspect, the present disclosure relates to a femoral hip implant. In a first example of a femoral hip implant embodiment, a femoral hip implant includes a neck and a stem extending from the neck. The stem includes a proximal portion and a distal portion, the proximal portion having a proximal anterior surface, a proximal posterior surface, a proximal medial surface and a proximal lateral surface. At a proximal end of the proximal portion, a first dimension of the stem from the proximal medial surface to the proximal lateral surface is in a range from 1.8 times to 2.2 times that of a second dimension of the stem from the proximal anterior surface to the proximal posterior surface. The proximal anterior surface is oriented relative to the proximal posterior surface at a first angle of 6.5 degrees or greater. The stem also includes a distal anterior surface and a distal posterior surface in the distal portion. The distal anterior surface is oriented relative to the distal posterior surface at a second angle of 4.5 degrees or greater, the second angle being less than the first angle.

In a second example, the proximal portion of the stem of the first example of the femoral hip implant may extend over a first distance and the distal portion of the stem may extend over a second distance such that the first distance combined with the second distance defines a length of the stem, the first distance being in a range from 8.2% to 10.4% of the length of the stem. In a third example, the first distance of the first example of the femoral hip implant may be between 9 mm and 11 mm. In a fourth example, any one of the first through third examples of the femoral hip implant may have a difference between the first angle and the second angle that is in a range from 0.4 degrees to 2.1 degrees. In a fifth example, the first angle of any one of the first through fourth examples of the femoral hip implant may be in a range from 6.5 degrees to 7.0 degrees. In a sixth example, the second angle of any one of the first through fifth examples of the femoral hip implant may be in a range from 4.5 degrees to 6.6 degrees.

In a seventh example, any one of the first through third examples of the femoral hip implant may be structured such that when the stem has a length less than 100 mm, a difference between the first angle and the second angle is 2.0 degrees or more. In an eighth example, any one of the first through third examples of the femoral hip implant may be structured such that when the stem has a length less than 113 mm, a difference between the first angle and the second angle is 1.0 degrees or more. In a ninth example, any one of the first through eighth examples of the femoral hip implant may be structured such that at a location at or distal to a transition between the proximal and distal portions, a third dimension of the stem from a distal medial surface to a distal lateral surface is in a range from 1.0 times to 1.8 times that of a fourth dimension of the stem from the distal anterior surface to the distal posterior surface. In a tenth example, the stem of the ninth example of the femoral hip implant may have a length in a range from 93 mm to 109 mm and the first dimension may be in a range from 1.8 to 2.0 times that of the second dimension. Further, the third dimension may in a range from 1.0 to 1.5 times that of the fourth dimension. In an eleventh example, the stem of the ninth example of the femoral hip implant may have a length in a range from 99 mm to 113 mm. Further, the first dimension may be in a range from 1.9 to 2.1 times that of the second dimension and the third dimension may be in a range from 1.2 to 1.7 times that of the fourth dimension. In a twelfth example, the neck of any one of the first through eleventh examples of the femoral hip implant may include a collar extending medially therefrom.

In one aspect, the present disclosure relates to a kit. In one embodiment, a kit includes a broach and a femoral hip implant. The broach may have a proximal portion including flat edged cutting teeth and a distal portion including pointed cutting teeth circumferentially disposed thereon. The femoral hip implant may have a stem with a medial surface, a lateral surface, an anterior surface and a posterior surface. A maximum dimension between the medial and lateral surfaces at a proximal end of the stem may be in a range from 1.8 times to 2.2 times a maximum dimension between the anterior and posterior surfaces at the proximal end.

In one aspect, the present disclosure relates to a method of designing a broach. In a first example of an embodiment of such a method of designing a broach, the method involves the following steps: determining a size of a femur to receive the broach; retrieving a plurality of medial-lateral dimensions of the femur, each of the plurality of medial-lateral dimensions being measured transverse to a length of the femur and being located at different locations along a length of the femur; identifying an anatomical transition region along the length of the femur based on at least a comparison of each of the plurality of medial-lateral dimensions; comparing the broach with the femur by viewing the broach in an implanted position in the femur and identifying a transition region on the broach that is coincident with the anatomical transition region; including a first plurality of teeth on a distal surface of the broach distal to the transition region, the first teeth having pointed protrusions; and including a second plurality of teeth on a proximal surface of the broach proximal to the transition region, the second plurality of teeth being different from the first plurality of teeth.

In a second example, the comparison step of the first example of the method of designing the broach may include the comparison of each of the plurality of medial-lateral dimensions and involve identifying a rate of change in the medial-lateral dimension of the femur along its length. The anatomical transition region may be identified as being located where the range of change of the medial-lateral dimension is between 0.2 mm per 10 mm length of the femur and 0.4 mm per 10 mm length of the femur. In a third example, the first example of the method of designing the broach may include retrieving a plurality of anterior-posterior dimensions of the femur, each of the plurality of anterior-posterior dimensions being measured transverse to a length of the femur and at the same locations as the plurality of medial-lateral dimensions. The method then proceeds with identifying an anatomical transition region along the length of the femur based on a comparison of each of the plurality of medial-lateral dimensions with the plurality of anterior-posterior dimensions, the anatomical transition region being located where the anterior-posterior dimension decreases to below 1.2 times the medial-lateral dimension in a proximal to distal direction.

In a fourth example, the determining step of any one of the first through third examples of the method of designing the broach may include aggregating a plurality of femur geometries into a representative femur to determine the size of the femur to receive the broach. In a fifth example, the fourth example of the method of designing the broach may involve a predetermined range of femur lengths to define the plurality of femur geometries. In a sixth example, the fifth example of the method may be performed such that the plurality of femur geometries are all dimensioned to receive a single broach size.

In one aspect, the present disclosure relates to a method of determining a geometry of a femoral hip implant. In a first example of one embodiment of such method, the method steps are as follows: receiving a geometry of a bone receiving the hip implant; at a first location between a neck of the bone and a lesser trochanter of the bone, taking a first planar section of the bone and determining a first medial extremity, a first lateral extremity, a first anterior extremity and a first posterior extremity, at a second location distal to the first location, taking a second planar section of the bone and determining a second medial extremity, a second lateral extremity, a second anterior extremity and a second posterior extremity, determining a first medial-lateral dimension of a stem of the hip implant at a medial proximal end of the stem as approximating a measurement from the first medial extremity to the first lateral extremity; determining a first anterior-posterior dimension of the stem of the hip implant at the medial proximal end of the stem as being between 40% and 60% of the first medial-lateral dimension; and determining a second medial-lateral dimension of the stem at a distal location on the stem closer to a distal end of the stem than the proximal end as being less than a measurement from the second medial extremity to the second lateral extremity such that the femoral hip implant in an implanted condition does not contact cortical bone of the bone at the distal location.

In a second example, the first example of the method of determining the geometry of the hip implant may include determining a second anterior-posterior dimension of the stem at the distal location on the stem, the second anterior-posterior dimension being between 50% and 100% of the second medial-lateral dimension. In a third example, the first or second example of the method of determining the geometry of the hip implant may include determining a first angle between anterior and posterior surfaces of the implant at the proximal end of the stem and determinizing a second angle between anterior and posterior surfaces of the implant at the distal location, the first angle being greater than the second angle. In a fourth example, the third example of the method of determining the geometry of the hip implant may be performed such that the anterior and posterior surfaces at the first angle extend to a transition depth approximately 9-10% of a distance from the proximal end of the stem to the distal end of the stem such that anterior and posterior surfaces distal to the transition depth are at the second angle. In a fifth example, any one of the first through fourth examples of the method of determining the geometry of the hip implant may be performed such that prior to receiving the geometry of the bone, a determination of a representative bone is made based on a plurality of bones grouped together based on a shared characteristic, the determined representative bone being used as the geometry of the bone. In a sixth example, the fifth example of the method of determining the geometry of the hip implant is performed such that the shared characteristic is a physical size range.

In one aspect, the present disclosure relates to a method of preparing a femur to receive a hip implant. In a first example of one embodiment of the method of preparing the femur, the following steps are performed: retrieving a broach with a proximal portion and a distal portion, the distal portion having a plurality of pointed teeth; driving the broach into a femoral canal accessible through a resected end of the femur creating an open volume to receive the hip implant; and inserting the hip implant into the open volume such that a proximal-medial surface and a proximal-lateral surface of the hip implant engages cortical bone of the femur while a distal most region of the hip implant is spaced apart from cortical bone of the femur.

In a second example, the first example of the method of preparing the femur may involve inserting the hip implant into the open volume to leave a proximal anterior surface and a proximal-posterior surface spaced apart from cortical bone of the femur such that no anterior or posterior surfaces of the hip implant engage cortical bone. In a third example, the first or second example of the method of preparing the femur may include: clearing bone material from a diaphyseal portion of the femur with the plurality of pointed teeth on the broach; clearing cortical bone material from medial and lateral sides of the femur in a metaphyseal portion of the femur; and compacting bone material from anterior and posterior sides of the femur in the metaphyseal portion of the femur.

In one aspect, the present disclosure relates to a method of designing a collar for a femoral hip step. In one embodiment, the method involves: determining a size of a femur to receive the femoral hip implant; selecting a femoral hip implant size based on the determined size of the femur;

visualizing the femoral implant implanted in the femur and determining a first distance from a central axis of the femur to a medial-most point on a stem of the femoral implant. And, while continuing to visualize the femoral implant implanted in the femur, determining a second distance from the medial-most point on the stem to a medial cortical bone surface of the femur, the second distance being a dimension of the collar as extending from the stem.

In some examples of the method of designing the collar, the medial cortical bone surface may be an outer cortical bone surface.

BRIEF DESCRIPTION OF THE DRAWINGS

The present disclosure will be better understood on reading the following detailed description of non-limiting embodiments thereof, and on examining the accompanying drawings, in which:

FIGS. 2 and 3 are side views of the broach of FIG. 1.

FIGS. 8-9 are side views of the hip implant of FIG. 7A.

FIGS. 12-13 illustrate a step in a method of designing a broach according to some embodiments of the present disclosure.

FIGS. 21-22 are front and side views of a hip implant according to an embodiment of the present disclosure.

DETAILED DESCRIPTION

Figure 1:
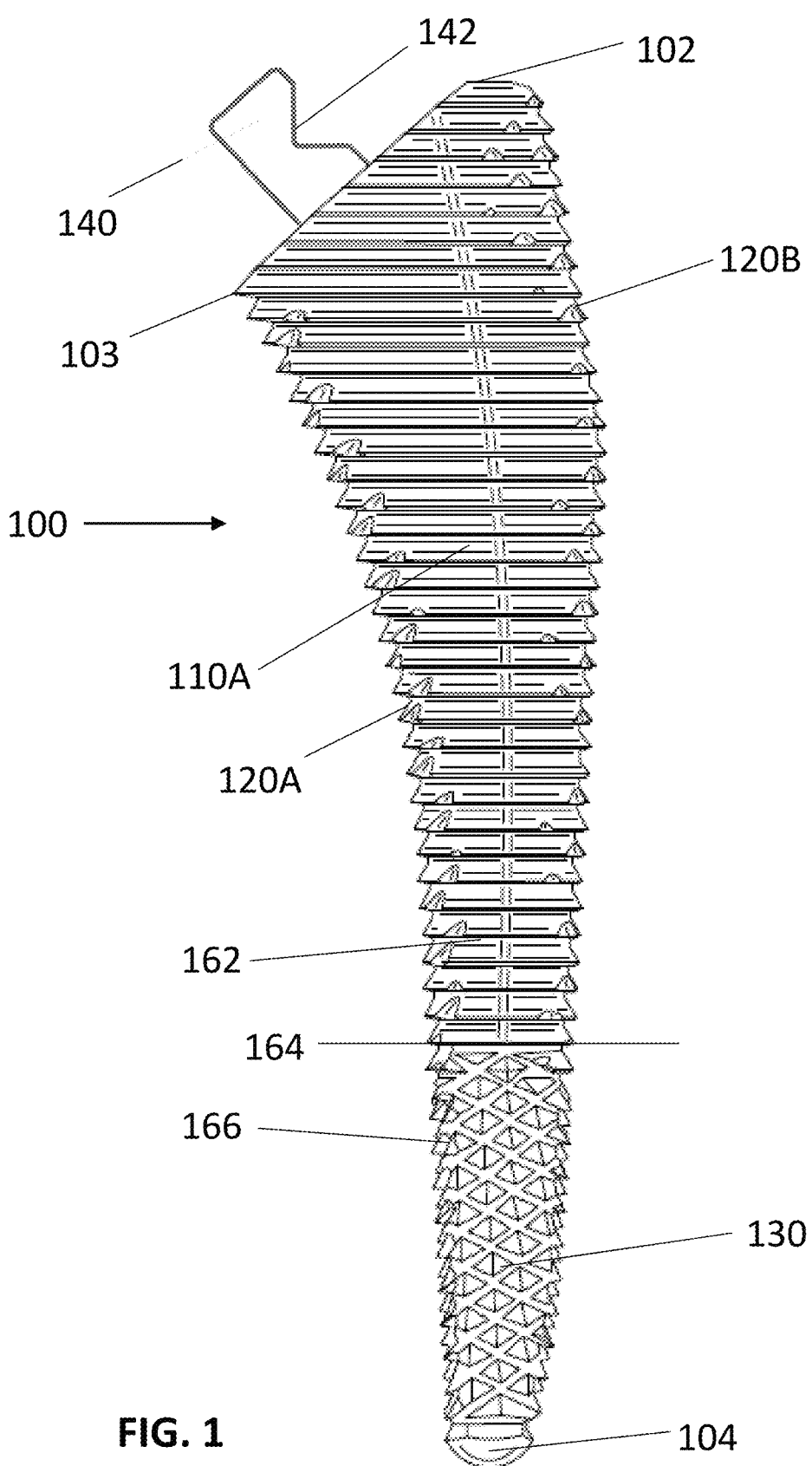
FIG. 1 is a front view of a broach according to one embodiment of the present disclosure.

Various embodiments will now be described in detail with reference to the drawings. In the drawings and in the description that follows, the term "proximal" refers to the portion of the instrument, implant or other device that is closest to the operator, while the term "distal" refers to the portion of the device that is furthest from the operator. Additionally, in the drawings and in the description that follows, terms such as front, rear, upper, lower, top, bottom, and the similar directional terms are used simply for convenience of description and are not intended to limit the disclosure attached hereto. In addition, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

The present disclosure describes instruments, implants, kits, methods of designing instruments and implants, and methods of using instruments and implants in hip surgery.

In one aspect, the present disclosure relates to a broach for use in creating an open volume to receive a femoral hip implant as part of a hip replacement procedure. One embodiment of such broach is broach 100 shown in FIGS. 1-3. In a proximal region of broach is a proximal end 102. Extending proximally from a proximal end 102 of broach 100 is an optional trunnion 140 with a recess 142 therein, the trunnion adapted to engagement with a tool for insertion of broach 100 into a femur. In some examples, the trunnion may have a different shape from that shown. In still further examples, other engagement features for engagement with an insertion instrument may be included at the proximal end of the broach.

A body of broach 100 extends between proximal end 102 and a distal tip 104 and includes a proximal region 162 and a distal region 166 separated by a transition region 164, shown in FIG. 1. In proximal region 162 anterior and posterior surfaces of the broach include compaction teeth 110A, 110B, where teeth indicated by reference numeral 110A are on the anterior facing surface and those indicated by reference numeral 110B are on the posterior facing surface in the example shown. With continued reference to proximal region 162, medial and lateral surfaces of the broach include extraction teeth 120A, 120B, where teeth indicated by 120A are on the medial facing surface and teeth indicated by 120B are on the lateral facing surface. In the illustrated example, these teeth cover an entirety of the respective surfaces in the proximal region. It should be appreciated that such comprehensive coverage is optional and that in other examples, only subportions of one or more of the respective surfaces may include the teeth as described.

Turning to distal region 166, separated from proximal region 162 by transition region 164, a surface around a full perimeter of the body includes a single aggressive cutting surface. As described above for the proximal region, the aggressive cutting surface may cover less than an entirety of the distal region. In the embodiment shown in FIGS. 1-3, the teeth in distal region 166 are diamond teeth 130. In other examples, other types of aggressive teeth may be included in the distal region. For example, the teeth may be spiked, pointed or acuminate with shapes other than that provided by the diamond teeth of the illustrated embodiment, shown in detail in FIGS. 6A and 6B. One reason the broach is designed this way is to avoid having excessively aggressive teeth in the proximal region of the broach. In this manner, a femoral canal surface left by the extraction and compaction teeth will mimic a surface of a femoral hip implant, while the aggressive teeth active in the distal region will not, where such correspondence between bone and implant surfaces is not as significant. These purposes are described in greater detail elsewhere in the present disclosure.

As already noted, transition region 164 separates the proximal and distal regions. A location of transition region 164 is determined using techniques as described elsewhere in the disclosure but is ultimately identified based on particular changes in characteristics of the bone receiving a hip implant over a length of the bone. The anatomical feature that characterizes this change is the transition between the metaphyseal region of the femur and the diaphyseal region of the femur, where the bone becomes more cylindrical. Femur measurements, for instance, those analyzed through data stored in the Stryker Orthopaedic Modeling and Ana- lytics (SOMA) database described in greater detail below, are used to determine where on the femur the rate of change in a medial-lateral width of the femur is approximately 0.3 mm per 10 mm. This location is then identified as transition region 164, and a distal region of the broach distal to the transition region will have diamond teeth. The distal region of the broach will penetrate a part of the femur with a relatively uniform lengthwise shape where a rate of change in the medial-lateral width is less than 0.3 mm per 10 mm and likely has a cylindrical shape. Transition region 164 may also be determined based on where a ratio of an anterior-posterior dimension of bone relative to the medial-lateral dimension reaches 1.0. In some examples, transition region 164 is located 60-80 mm below a proximal medial edge 103 of broach 100. In some examples, transition region 164 is located 50% to 70% of a distance from proximal medial edge 103 to distal tip 104. In further examples, transition region 164 is located 64% to 69% of a distance from proximal medial edge 103 to distal tip 104. In other examples, other distances may apply and may be guided by the anatomy of the femur under consideration.

Figures 4A, 4B, 5A, 5B, 6A, 6B:
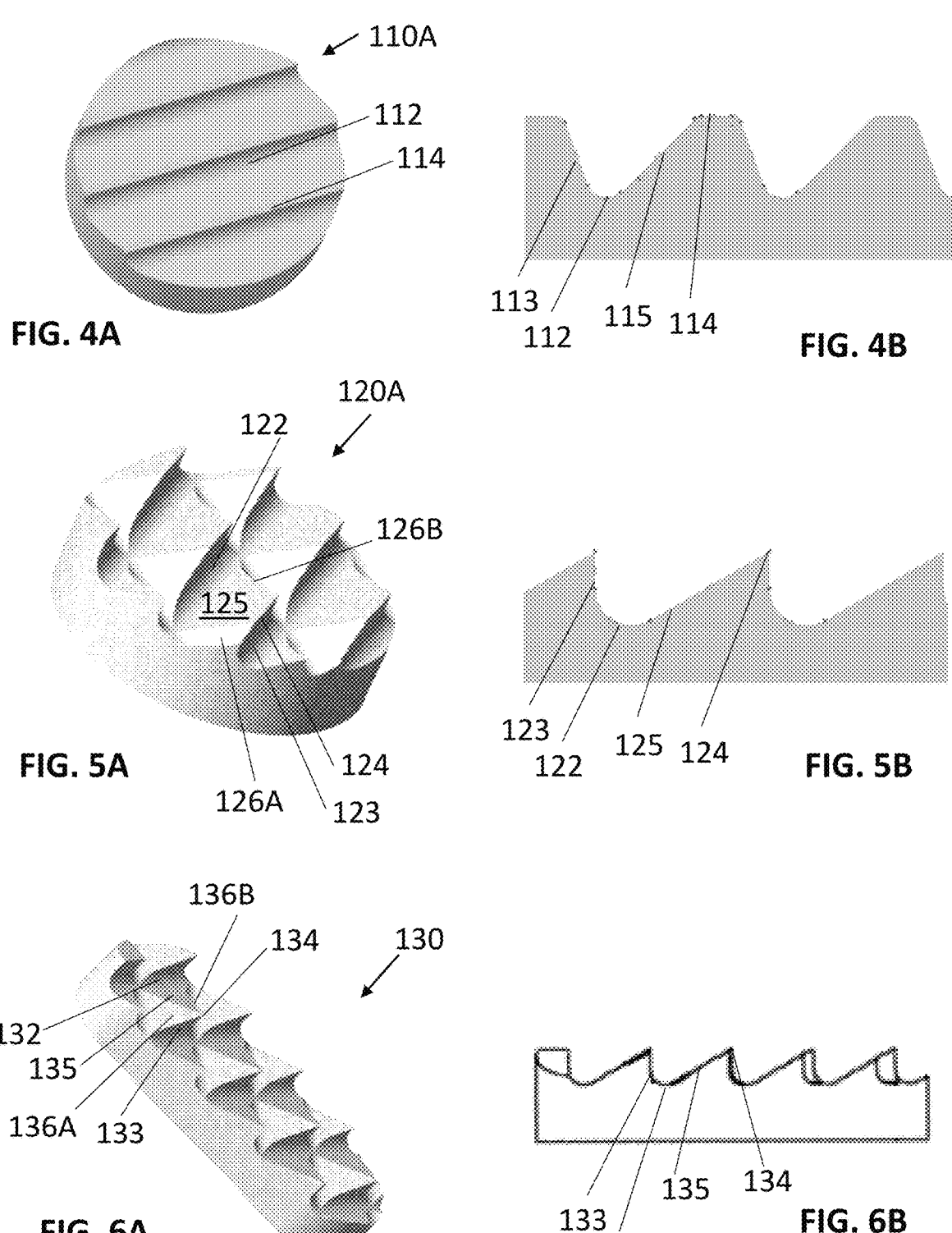
FIGS. 4A-4B are detailed views of compaction teeth of the broach of FIG. 1.
FIGS. 5A-5B are detailed views of extraction teeth of the broach of FIG. 1.
FIGS. 6A-6B are detailed views of diamond teeth of the broach of FIG. 1.

Details of the various teeth on broach 100 are shown in FIGS. 4A-6B. In particular, compaction teeth 110A are shown in FIGS. 4A-B, extraction teeth 120A are shown in FIGS. 5A-B and diamond teeth 130 are shown in FIGS. 6A-B.

Compaction teeth 110A include a pattern of repeating troughs 112 and protrusions with ends in the form of flat ridges 114. Troughs have rounded low points with a shallower angle on surface flank 115 approaching flat ridge 114 than on a leading surface 113 in front of a preceding flat ridge, as shown in FIG. 4B, though leading surface 113 is shallower than 90 degrees relative to an overall surface of the broach. As shown in FIG. 4A, flat ridges 114 have a length that extends in an unbroken fashion across a width of a surface region that includes the compaction teeth. The shape of the compaction teeth is such that they do not include a chip breaking function. In terms of performance, in use, compaction teeth 110A reduce the tendency to extract bone and improve bone compaction for greater stability.

Extraction teeth 120A have repeating troughs 122 and protrusions with ends in the form of ridges 124, where the ridges 124 have a sharp edge with a length, shown in FIG. 5A, that is shorter than a distance across trailing flank 125 from trough 122 to ridge 124, unlike the ridges of the compaction teeth. Rearward from trough 122 to a preceding ridge is a leading surface 123 of a preceding tooth. Each ridge 124 is abutted by four surfaces that protrude from troughs of the teeth. These include trailing flank 125, side surfaces 126A-B, and leading surface 123. An uppermost region of leading surface 123 approaching ridge 124 is oriented approximately 90 degrees relative to a surface of the broach, unlike leading edge 113 on compaction teeth 110A. The shape of the extraction teeth provides a chip breaking function that improves bone removal to create a surface in the bone that mimics the shape of the hip implant to be placed after use of the broach.

For diamond teeth 130, a surface progresses repeatedly from a trough 132 to a protrusion with an end in the form of protrusion tip 134, as shown in FIG. 6B. In a manner similar to extraction teeth, each protrusion tip 134 is abutted by four surfaces that protrude from surrounding troughs, such as trough 132. However, for diamond teeth 130, each of these surfaces converges at a point in the form of protrusion tip 134. The four surfaces include flank 135, side surfaces 136A, 136B and leading surface 133. These surfaces, shown in FIG. 6A, may also be understood as two flanks 135, 136A rising from the trough of the broach surface toward the protrusion tip, with two leading surfaces 133, 136B in front of the flanks. As with the extraction teeth, the diamond teeth promote cutting of bone, although diamond teeth 130 are distinguishable in their aggressiveness and are particularly well suited for bone removal in a diaphyseal region of a femur where a purpose of the teeth is not explicitly directed to aligning an implant surface with a remaining bone surface, since clearance is desired in this region. The uniquely shaped cutting surfaces of the diamond teeth are particularly well suited to remove bone at greater distances from an entry location into a bone.

The broach may be made of a metal material. For example, the broach may be titanium, a titanium alloy, stainless steel, a stainless steel alloy, or a cobalt chrome alloy (CoCr).

The broach is advantageous in that it provides bone preparation directed to specific locations in a femur, whether anterior-posterior sides of a proximal region, medial-lateral sides of the proximal region, or in the distal region. The extraction teeth on the medial-lateral sides of the broach improve bone removal, while the compaction teeth prepare cancellous bone for receipt of anterior-posterior sides of an implant. The diamond teeth at the distal end of the broach promote more aggressive bone removal and are adapted to enhance removal of bone, including cortical bone, in a diaphyseal section of the femur, where the bone profile is much narrower than in more proximal regions of the femur. With such removal, an entire length of an inner region of the femur expected to receive a hip implant is better prepared for a secure and stable fit in a planned position.

The broach may be varied in many ways. In some examples, a broach may include a single type of tooth on the proximal region along with diamond teeth on the distal portion. In some of these examples, the proximal region only includes compaction teeth. In others, the proximal region only includes extraction teeth. In still further examples, the broach only includes teeth in the distal region and those teeth are diamond teeth. Such a variation may be of use when the broach is being used specifically to target the diaphyseal region of the femur.

In another aspect, the present disclosure relates to a hip implant. One embodiment of such hip implant is implant 200 shown in FIGS. 7A, 8 and 9. It should be appreciated that references to implant are used interchangeably with stem or implant body throughout the disclosure. Implant 200 includes a neck 205 with a receiving portion 206 at a free end and a collar 207 on a medial side near an interface 202 with a stem of the implant.

The collar 207 extends from neck 205 such that it has a tapering shape towards a narrow lip 208 at its free end. The closest part of the body to collar 207 is at medial resection point 219, best shown in FIG. 7A. A distance between medial resection point 219 and lip 208 of collar 207 represents a length of collar 207. A distal face of collar 207 may optionally be planar between medial resection point 219 and lip 208. On a side of collar 207 extending into neck 205, collar has a concave surface toward receiving portion 206.

Figure 7A:
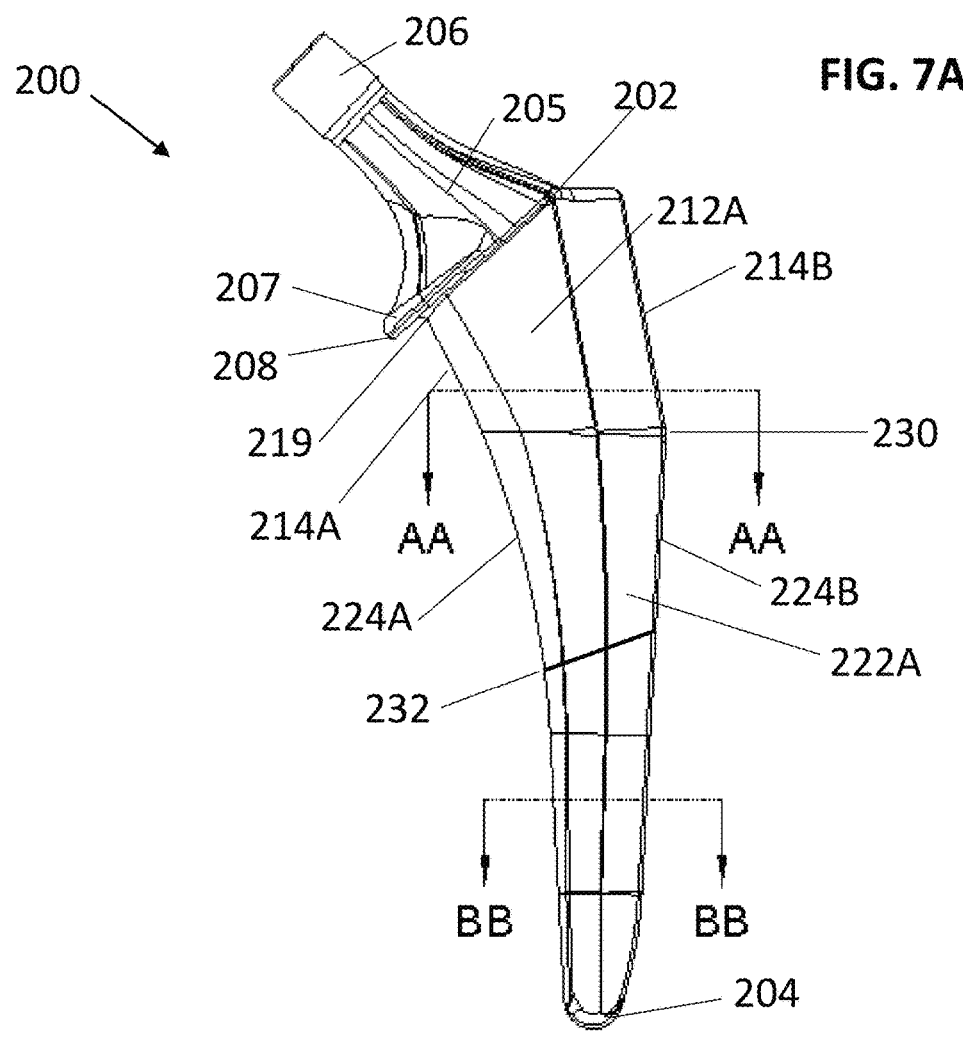
FIG. 7A is a front view of a hip implant according to one embodiment of the present disclosure.

The body of implant 200 includes anterior, posterior, medial and lateral surfaces that extend from interface 202 to distal tip 204. The body is separated at a transition depth 230 into a proximal region and a distal region. The proximal region has an anterior surface 212A, a posterior surface 212B, a medial surface 214A and a lateral surface 214B. The distal region has an anterior surface 222A, a posterior surface 222B, a medial surface 224A and a lateral surface 224B. In some examples, transition depth 230 corresponds to an elbow of the implant on the lateral side, as shown in FIG. 7A, and may be in a range from 7 to 11% of a distance from medial resection point 219 to distal tip 204. In other examples, transition depth may be in a range from 8 to 10% of the distance. In still further examples, it may fall within an overlapping or even non-overlapping range from the aforementioned ranges as a function of the patient bone anatomy, whether considered individually or as bone anatomy that is representative of the patient, such as may be retrieved from the SOMA database.

Figure 7B:
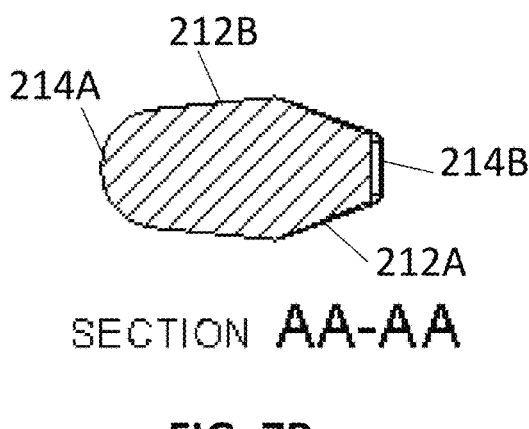
FIGS. 7B-7C are sectional views of the hip implant of FIG. 7A.
Figure 7C:
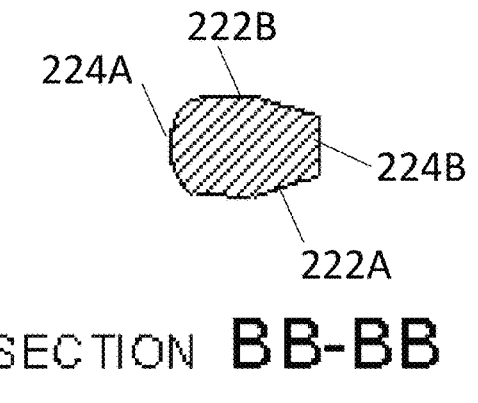

A profile of the body, or stem, viewed in a plane perpendicular to a length of the stem at one location in the proximal region is as shown in FIG. 7B while a profile of the body at one location in the distal region is as shown in FIG. 7C. It should be appreciated that the profile of implant 200 shown in FIGS. 7B and 7C is optional and in other examples may vary from the illustrated shape. With continued reference to the illustrated embodiment, in the proximal region, medial surface 214A is curved, anterior and posterior surfaces 212A, 212B each have two planar subparts that converge at an apex, and lateral surface 214B is planar. In the distal region, the medial surface 224A is curved with a radius larger than that present in the proximal region, anterior and poster surfaces 222A, 222B each have two planar subparts that converge at an apex, and lateral surface 224B is planar.

When viewed from the anterior side such that the length of the body is visible, as shown in FIG. 7A, medial surfaces 214A, 224A are curved in a concave manner and lateral surfaces 214B, 224B are planar with lateral surface 214B having a steeper angle than lateral surface 224B. Lateral surfaces 214B, 224B converge at an apex, or elbow, located at a transition depth 230 of implant 200 that separates the proximal and distal regions. When viewed from the medial or lateral side such that the length of the body is visible, as shown in FIGS. 8 and 9, anterior surfaces 212A, 222A and posterior surfaces 212B, 222B are planar in respective proximal and distal regions, though a slope of each surface changes at transition depth 230. In particular, when viewed from either a medial or lateral side of implant 200, surfaces 212A, 212B in the proximal region are angled relative to one another at proximal angle $\theta_1$ and surfaces 222A, 222B in the distal region are angled relative to one another at distal angle $\theta_2$. Proximal angle $\theta_1$ is greater than distal angle $\theta_2$. In some examples, proximal angle $\theta_1$ is in a range from 6.6 degrees to 7.0 degrees and is greater when a length of the body is longer. In some examples, distal angle $\theta_2$ is in a range from 4.5 degrees and 6.6 degrees and is greater when a length of the body is longer. As already stated, the proximal angle is greater than the distal angle, though this difference is less with longer implants. In some examples, the difference may be approximately 2.0 degrees, while in other examples, it may be closer to 1.0 degree.

Implant 200 may be made of a metal material. For example, the implant may be made of titanium, a titanium alloy, stainless steel, a stainless steel alloy, or a CoCr alloy. It should also be appreciated that implant 200 may optionally include a bone ingrowth coating. Such coating may be distributed on a surface of the body of implant 200 between the neck-body interface 202 and an ingrowth coating limit 232, shown in FIG. 7A. The bone ingrowth coating may be porous relative to a surface distal to ingrowth coating limit 232. In some examples, the bone ingrowth coating may be commercially pure titanium with a hydroxyapatite spray finish, which may be a 50-micron plasma spray. In other examples, the bone ingrowth coating may be Ti-6Al-4V. In further examples, instead of bone ingrowth coating, the surface in the bone ingrowth region may be hydroxyapatite roughed through grit blasting. In still further examples, the surface may be prepared through loose metal sintering, formed through sequential impregnation/dissolution of dissolved salts to create a foam structure, or additively manufactured to create a three-dimensional porous surface. For the region below the ingrowth coating limit 232, the surface may be coated with hydroxyapatite. The hydroxyapatite coating may be grit-blasted. In further examples, the implant may have no hydroxyapatite coating, may have a satin finish that is smooth, or may be formed through grit blasting. Any of the above examples may be varied such that regions on either side or both sides of the ingrowth coating limit may have no hydroxyapatite coating.

With continued reference to the body of implant 200, we turn to relative dimensions, specifically, a ratio between a medial-lateral dimension and an anterior-posterior dimension, hereinafter referred to as an ML:AP ratio. At the medial resection point, the ML:AP ratio may be in a range from 1.8 to 2.2. The ML:AP ratio may be larger for larger implants. Thus, for example, an implant of a smaller size having a length of approximately 90 mm may have an ML:AP ratio in a range from 1.75 to 1.85. For an implant with a length of approximately 120 mm, an ML:AP ratio may be in a range from 2.15 to 2.25. Closer to distal tip 204 of implant 200, the ML:AP ratio is smaller. At an ingrowth coating limit 232, shown in FIG. 7A, the ML:AP ratio may be in a range from 1.0 to 1.8, where larger implants have larger ML:AP ratios at this level of the implant.

Implant 200 has a body shape such that engagement to bone in the proximal region is optimized. In particular, the ML:AP ratio in the proximal region provides an implant with enhanced medial-lateral engagement with cortical bone, while leaving space in an anterior-posterior direction for compaction with cancellous bone. Additionally, the ratio of the stem dimensions itself optimizes performance and stability. The anterior-posterior dimension is designed to fill a significant amount of space in that direction, while at the same time not superseding the desired medial-lateral engagement. This preserves the stability of the implant when subject to expected forces after surgery. And, the degree to which the femoral canal is filled in the AP direction improves stability. Further, the changing ML:AP ratio toward distal tip 204 of the implant allows for disposal of the implant in a femur with clearance from cortical bone, or put another way, with minimal engagement with cortical bone, in the distal region. The varying slope between the proximal angle of the proximal anterior and posterior surfaces and the distal angle of the distal anterior and posterior surfaces further enhance the above-described advantages. An additional advantage that should be appreciated is that the combination of fixation at proximal medial and proximal lateral sides, in combination with clearance in the distal region, improves performance of the implant relative to having only one of the design features. Further advantages include that the collar is sized to fit over the bone with minimal overhang. This is described in greater detail elsewhere in the disclosure.

Implant 200 may be varied in many ways. One alternative embodiment is implant 200' shown in FIGS. 21-22, where the 200' series of reference numerals refer to like elements in the 200 series of reference numerals unless otherwise noted. For implant 200', transition depth 230' is located further from the neck of the implant than the arrangement illustrated in FIG. 7A. In the illustrated example of such embodiment, the transition depth 230' corresponds to the ingrowth coating limit 232'. In this manner, the proximal anterior and posterior surfaces 212A', 212B' have proximal angles, measured based on an angle between the surface and a central longitudinal axis of the implant, that extend from the neck-body interface 202' to the ingrowth coating limit 232' while the distal anterior and posterior surfaces 222A', 222B' have distal angles that extend from the ingrowth coating limit 232' to the distal tip 204' of the implant. As with other embodiments, the proximal angle is greater than the distal angle.

In other embodiments, a transition depth of a hip implant may be located at other locations along a length of the implant body. In some examples, this may be at a location in between that of the embodiment shown in FIG. 7A and the embodiment shown in FIG. 21. In other embodiments, a hip implant may have an offset that is increased or decreased relative to an offset of implant 200 to accommodate the needs of certain patients. Here, offset means a distance between a femoral head center and a central femoral axis.

In another aspect, the present disclosure relates to a hip surgery kit including one or more items such as a broach and a femoral hip implant. In one embodiment, a kit may include two or more femoral hip implants. In some examples, the two or more hip implants include two or more hip implants that are the same size. In other examples, the two or more hip implants include two or more hip implants that are different sizes. In one embodiment, a kit may include two or more broaches. In some examples, the two or more broaches include two or more broaches that are the same size. In other examples, the two or more broaches include two or more broaches that are different sizes. In one embodiment, a kit may include one or more broaches and one or more femoral hip implants. In some examples, at least one of the broaches and at least one of the femoral hip implants are the same size. In other examples, at least one of the broaches and at least one of the femoral hip implants are different sizes. In some embodiments, the two or more hip implants may include two hip implants of the same size but different medial offsets. In any one of the above embodiments, the kit or individual items and combinations thereof may be disposed within a package or a plurality of packages. For example, all of the items of the kit may be disposed within a single package. In another example, all of the broaches may be in one package and all of the hip implants in another. The items included in the kit may also be individually packaged. For example, each broach may be in its own package. Packaging each item in the kit separately or in different combinations may improve the sterility of the items in preparation for and during surgery. One reason for this is that some items may be required prior to others when implanting the hip implant. For example, the hip implant could remain in its own package while the broach is used. In any of the above embodiments, a kit may further include an instruction manual with an explanation of details relating to the contents of the kit including instructions for use of the contents.

In other aspects, the present disclosure relates to methods of designing a broach or a femoral hip implant. We begin with an initial step in the process that applies for both broach and implant design and involves establishing a reference geometry of a bone to receive a respective broach or an implant. In some embodiments, morphological bone data, also referred to as bone data, such as bone data for the femur, is collected from across an assortment of demographic profiles, which are first sorted into groups and then analyzed for each group to design a broach or implant. One vehicle to realize this collection and analysis is optionally through use of the SOMA database. In one example, SOMA collects and stores femur dimensions of a large number of individuals, where the information may be sourced from CT scans of such individuals. References to SOMA data of the SOMA database are made throughout the disclosure for ease of explanation though it should be appreciated that data aggregation techniques other than SOMA may also be used for the designs described in the various embodiments of the present disclosure. Additionally, it should also be appreciated that the methods described in this disclosure are not limited to reliance on aggregated data for a reference bone geometry. However, if a design is made for a specific individual, it would of course have limited, if any, use for a wider group of individuals.

The large volume of patient data available through SOMA may be retrieved and analyzed to provide an output that may be used to guide designs. For the broach and hip implant in particular, femur images and other source data are collected for a large number of individuals of varying demographic profiles. Such information may be analyzed using statistical modeling and, based on the determined characteristics of the femur of each individual in the data set, may be placed into groups based on shared characteristics. One way the groups may be established is by including all femurs for which a particular estimated implant size fits into a single group and doing the same for other estimated implant sizes. In one variant, the data for each femur may be evaluated to determine what size stem would fit in the medial-lateral aspect. Another way the groups may be defined is by size of the femur. As one very simple example, all data for femurs between 400 mm and 450 mm in length may be assigned to a first group, all data for femurs between 450 mm and 500 mm in length may be assigned to a second group, and all data for femurs between 500 mm and 550 mm in length may be assigned to a third group, and so on. Of course, other length ranges may be used to group the source data as desired.

Figure 10:
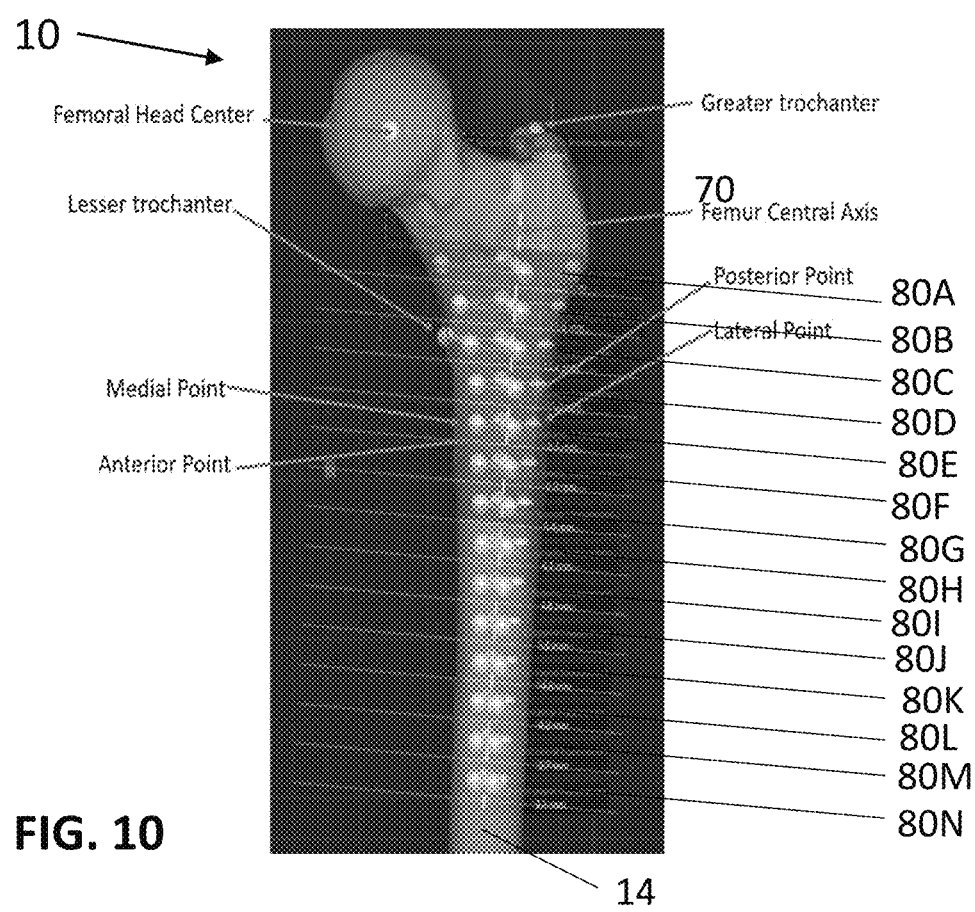
FIGS. 10-11 illustrate a step in a method of designing a broach or hip implant according to some embodiments of the present disclosure.
Figure 11:
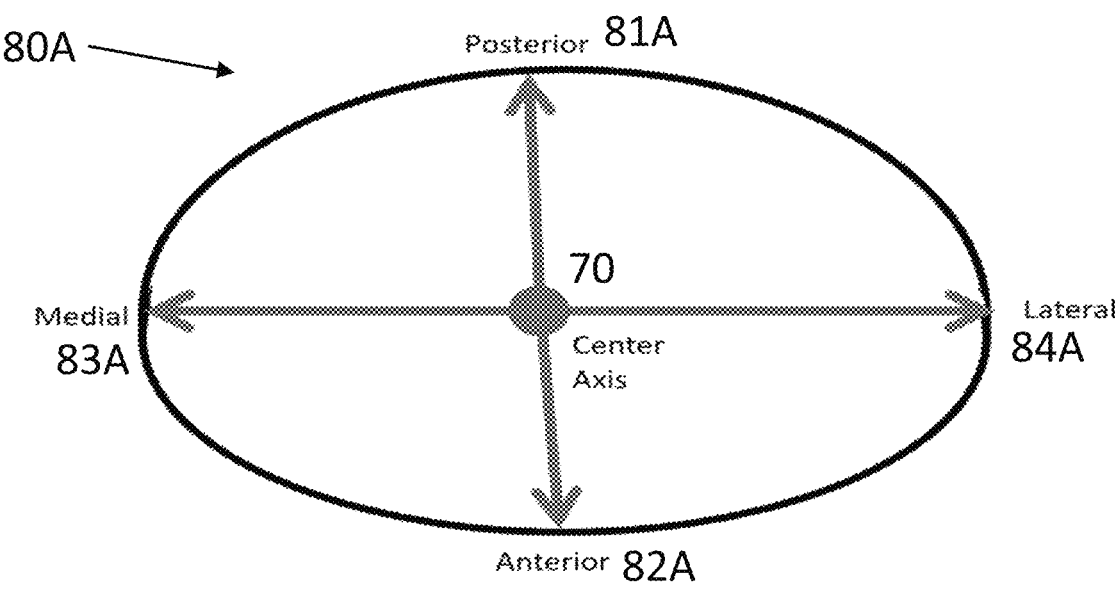

Once the source data is assigned to an applicable group, each femur within the group is analyzed in detail to identify and store certain dimensions of the femur for use in the design process. In some embodiments, a central longitudinal axis 70 and medial, lateral, anterior and posterior extremes in each of a plurality of transverse planes 80A-80N are identified, as shown in FIGS. 10-11 for femur 10, where each transverse plane is perpendicular to central longitudinal axis 70. Identification of coordinates for each of the aforementioned extremities is performed at regular intervals along a length of the femur through the diaphysis and through at least part of the metaphysis, as shown in FIG. 10. FIG. 11 illustrates representative anatomical information identified and stored at each transverse plane via the information retrieved from transverse plane 80A. At plane 80A, coordinates of a location of the central longitudinal axis 70 are identified and stored, along with coordinates of a medial-most point 83A on the bone, a lateral-most point 84A, a posterior-most point 81A and an anterior-most point 82A. The identified coordinates may be three-dimensional cartesian coordinates. In some examples, the transverse planes may be located at 10 mm intervals along a portion of the femur. In those and other examples, the transverse planes may be located at intervals relative to an anatomic feature, such as the lesser trochanter. In such cases, the transverse planes may be located at 10 mm multiples from the lesser trochanter, and one of the transverse planes may pass through the lesser trochanter itself. Once all data points are identified and stored for the femur, the process is repeated for each of the other femurs assigned to the group under consideration.

With SOMA-derived data points stored for each femur in an assigned group, the data points are analyzed determine femur dimensions and landmarks that are representative of all of the femurs in the group. Thus, a representative femoral axis is based on combining data for the femoral central axis of each femur in the group. In one example, the representative femoral central axis is based on an average of the femoral central axis for each femur. Similarly, representative medial-most, lateral-most, posterior-most and anterior-most points, for example, points 83A, 84A, 81A, 82A, at each transverse plane 80A-80N, are based on combining data for such points on each femur in the group. As above, the representative points at each transverse plane may be based on an average of the points identified for each femur. Upon completion of this processing step, each group has a set of data points that are representative of the femurs in that group.

In some embodiments, a method of design relates to a method of designing a broach. In one embodiment of the method, design of a broach begins with a design of a femoral implant, as described below for the implant shown in FIGS. 14-20. The geometry of the femoral implant design is then used to establish the geometry of the broach. Optionally, specific surfaces on the broach may be adjusted relative to the hip implant design to achieve particular press-fit performance and clearance with the broach disposed in a femur. In another embodiment of the method, design of the broach involves collection of bone data from a collection of individuals, sorting of the data into groups, and then analysis of the data for each group to generate a data set that is representative of the data derived from all individuals assigned to the respective groups. One exemplary way this is accomplished is through the use of SOMA data, as described in detail above. It should be appreciated that the groupings for any particular design process may encompass only a single group or may include multiple groups. Each group is based on a range of femur lengths, but it is contemplated that other considerations may be used to determine an assigned group for the source data.

Whether the broach geometry is established by the femoral implant design or based on SOMA data, the SOMA data may be used to determine transition region 164 that separates different types of cutting surfaces. To design cutting surface regions of a broach for each group of femurs (e.g., a group representative of a size range), a medial-lateral dimension is obtained from the medial-most and lateral-most points at each transverse plane from among multiple transverse planes along a length of a representative bone geometry. These measurements are compared with the others by moving along a length of the representative bone from one end to the other. The purpose of this comparison is to capture a change in the characteristics of the femur along its length. A typical femur has a medial flare 18 in a metaphyseal region that tapers and becomes flatter and closer to collinear with central longitudinal axis 70 in a diaphyseal region, as shown in FIG. 12, for example. This characteristic is used in conjunction with the SOMA derived data points to determine when a rate of change in a width of the bone approaches 0.3 mm per 10 mm length moving either proximally or distally. The exact rate of change of width per unit length may vary to make a final design consistent with designs for other broach sizes or for other circumstances that may apply. For instance, a target rate of change may be modified to 0.25 mm per 10 mm length or 0.35 mm per 10 mm length. One example of the rate of change in a medial-lateral dimension of a femur along its length is shown by the extrapolation of a collection of data from the SOMA database in the chart of FIG. 13.

When the transition between metaphyseal and diaphyseal regions is determined by analysis of the data, the location is identified as a transition region such as transition region 164 in FIG. 1 and represents where the cutting teeth on the broach change between compaction/extraction teeth and diamond teeth. Because this analysis is performed for data on a group-by-group basis, a location of such transition region on a broach may differ, and very likely differs, between groups of data points that are distinguished by femur size or other characteristics. In a study, data representative of a group of individuals retrieved from the SOMA database was used to implement the described approach to determine a transition region on the broach. In the study, the SOMA database included CT scans of femurs of over 1300 individuals. Through analysis of the data, a transition region was estimated for each of eleven different femur size ranges. The results of that analysis are summarized in Table 1 below.

TABLE 1

| Femur Size Grouping (estimated broach length) | Distance to estimated transition region (mm below medial resection point) | Percentage of broach length above transition region (%) |
|---|---|---|
| 0 (93 mm) | 60 | 65 |
| 1 (96 mm) | 60 | 63 |
| 2 (99 mm) | 60 | 62 |
| 3 (101 mm) | 60 | 60 |
| 4 (103 mm) | 60 | 59 |
| 5 (105 mm) | 60 | 57 |
| 6 (107 mm) | 70 | 65 |
| 7 (109 mm) | 70 | 64 |
| 8 (111 mm) | 70 | 63 |
| 9 (113 mm) | 80 | 70 |
| 10 (115 mm) | 80 | 68 |
| 11 (117 mm) | 80 | 67 |

As an additional optional step in the design method, the distance to the transition region may be modified to accommodate any need for consistency among broaches of varying sizes. Thus, for example, the above described dimensions may be modified so that a transition region is located at incrementally greater distances from the medial resection point for progressively larger implant sizes. In one illustrative example that utilizes the estimated transition regions in Table 1, a distance to the transition region for size 0 may be 65 mm and increase in 1 mm increments up to size 11, which would have a distance of 76 mm.

In a variation of the method of designing a broach, the SOMA data is analyzed to determine where a ratio between an anterior-posterior dimension of the femur to a medial-lateral dimension of the femur approaches 1.0 when moving in a distal direction. Ratios based on representative data at each transverse plane, e.g., medial-most, lateral-most, anterior-most and posterior most points, may be used in the analysis, where the AP:ML ratio is expected to be higher than 1 in the metaphysis while decreasing toward the diaphysis. When a location along a length of the femur having an AP:ML ratio approaching or near 1.0 is determined, such location is set as the transition region between the compaction/extraction teeth and the diamond teeth based on the broach being fully inserted into the femur as would occur during use of the broach.

In one embodiment, a method of design relates to a method of designing a femoral hip implant, as shown, for example, in FIGS. 14-20. In the method, femur bone data is collected from a collection of individuals, sorted into groups, and then the data is analyzed for each group to generate a data set that is representative of all individuals assigned to the respective groups. One exemplary way this is accomplished is through the use of SOMA data, as described in detail above. As with the broach design, representative data points for each group are used to design a hip implant for such groups. Specifically, this may involve the determination of representative data points for each group where each group represents a range of femur sizes or another shared characteristic.

The representative data for each group may include a femoral central axis and anatomical points on a series of transverse planes through the femur, as described above and shown in FIGS. 10 and 11. The following description is for the design of one hip implant for a femur that falls within a single group that represents a range of femur sizes, but it should be appreciated that the design for other groups may be performed in the same way, albeit with different data analysis in view of the different femur size information. Additionally, as already noted, a characteristic other than size may also be used.

Figures 14, 15, 16:
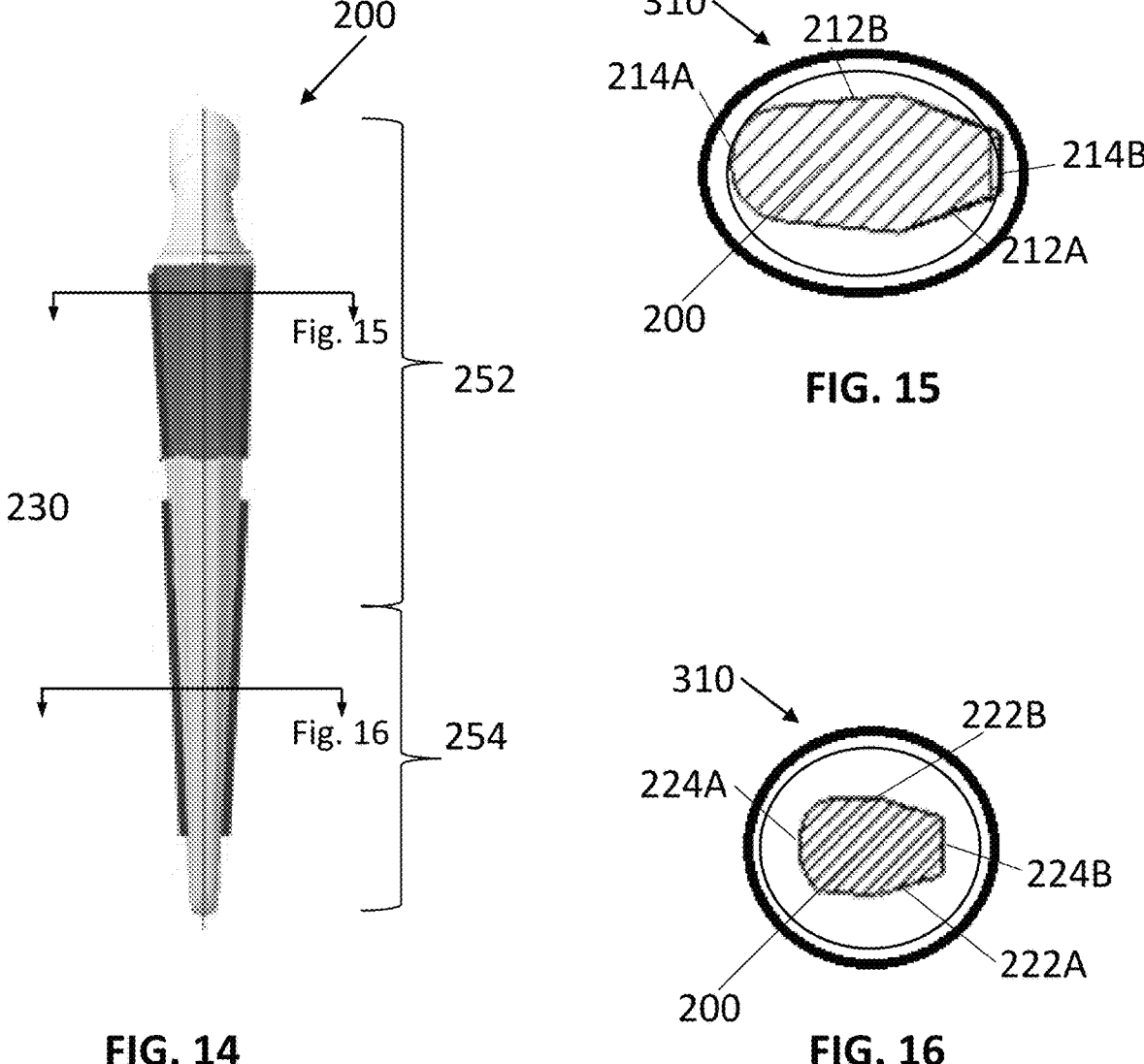
FIGS. 14-16 are side and sectional views of a hip implant in a step of a method of designing the hip implant according to some embodiments of the disclosure.
Figure 17:
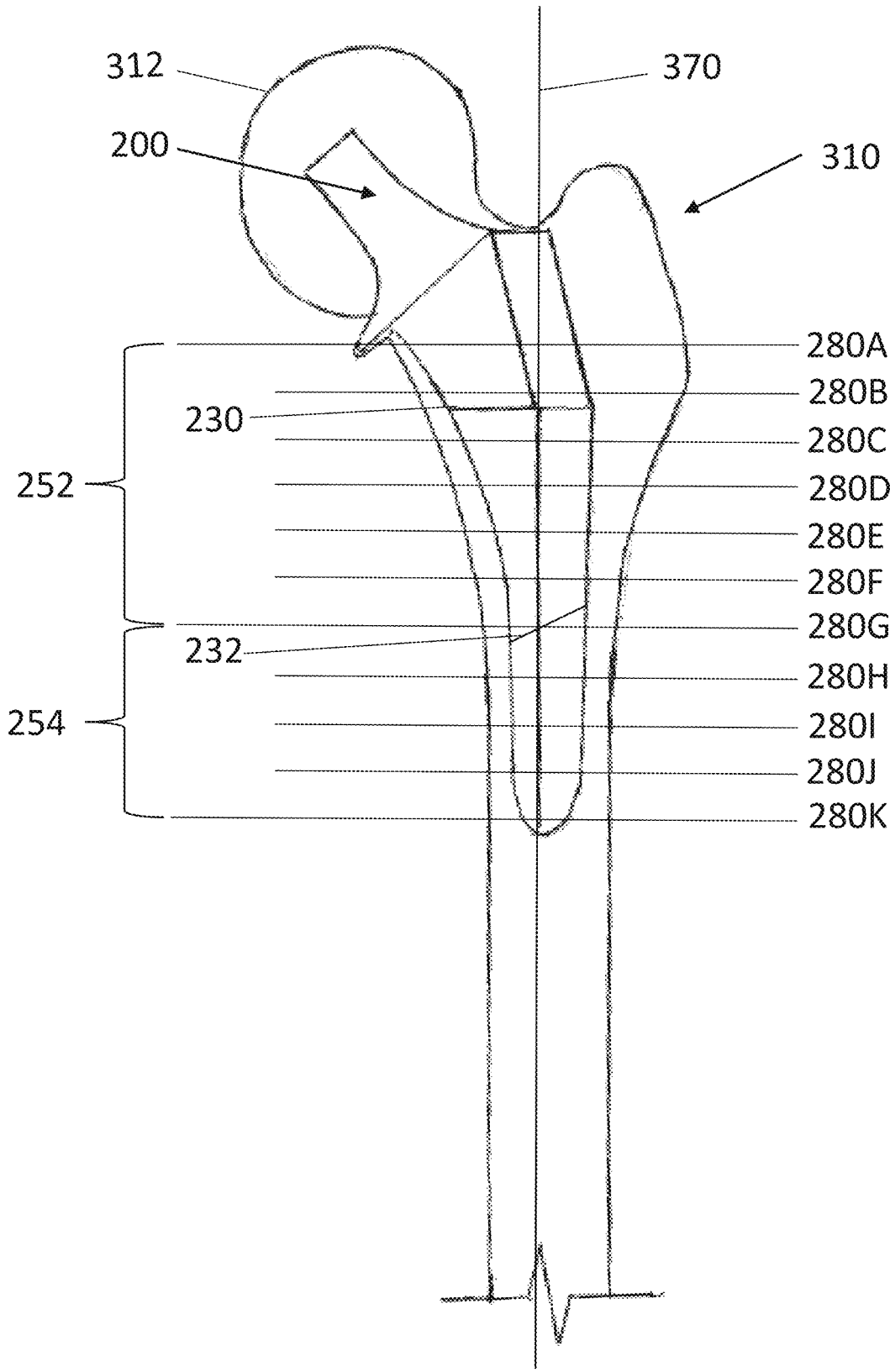
FIGS. 17 and 18 are front and side views of a hip implant in a step of the method of designing the hip implant according to the embodiment of FIGS. 14-16.

Initially, a dimension from a medial-most point to a lateral-most point is determined at each transverse plane. For the femur group under consideration in the present embodiment, that is transverse planes 280A-280K shown in FIGS. 17 and 18. The medial-most and lateral-most points are locations on the anatomy, here, on the femur bone, as described in the description accompanying FIGS. 10 and 11. One part of the implant design process involves determining a ratio between a medial-lateral dimension and an anterior-posterior dimension at different locations along a length of the implant. Because the design advantageously provides cortical bone engagement in a more proximal part of the implant and provides clearance from cortical bone in a non-overlapping distal part of the implant, this part of the design process can be broken up into two substeps: A first step to design for an engagement region 252 and a second step to design for a clearance region 254. These regions are shown in FIGS. 14 and 17. During the implant design process, the SOMA data may be analyzed to estimate an optimal position of the implant via SOMA-based femoral hip centers, femoral medial resection points and femoral central axes. In this manner, the sizing of the implant may be determined in a manner that is best aligned with an expected implanted position of the implant.

The engagement region 252 approximately coincides with a portion of the implant that includes ingrowth coating or another engagement surface as contemplated in the present disclosure. In one embodiment, a proximal-distal extent of the engagement region 252 is based on surface engagement regions included in previously developed hip implant designs, such as that included in the hip implant of the Stryker® Accolade® II system. The distal extent of the engagement region 252 ultimately approaches the juncture between metaphyseal and diaphyseal regions but remains within the metaphyseal region. In another embodiment, determination of the engagement region 252 may be based on data from the SOMA database that is analyzed and then used to identify a physical extent of the metaphyseal part of the femur. By identifying a physical extent of the metaphysis, a determination can be made as to the portion of the implant that will be located in the engagement region within the metaphyseal part when the implant is disposed in the femur. To convert information about the femur to information about the hip implant, the hip implant may be overlaid on the femur. Methods of identifying the metaphysis may be those methods described for the design of the broach above. In one example, a limit of the metaphyseal part of the femur, at a transition to the diaphyseal part, is established as a location where the rate of change of a width of the medial-lateral dimension reaches 0.3 mm per 10 mm of length. For the purposes of this explanation, such location in FIG. 17 is found at transverse plane 280H, slightly distal to ingrowth coating limit 232 of implant 200 determined to approximately correspond to transverse plane 280G. Thus, above transverse plane 280G the implant is expected to engage with the cortical bone of the femur on the medial and lateral sides that are shown in FIG. 17.

The dimensions of the implant for engagement region 252 are established by first identifying the medial-lateral dimension of the femur at each transverse plane 280A-280G in engagement region 252. Because hip implant 200 is intended to engage cortical bone on the medial and lateral sides in this engagement region, the medial-lateral dimension of the implant is sized to measure close to or slightly greater than a distance between cortical bone surfaces in the medial-lateral direction along a length of engagement region 252. One exemplary section cut in this region is shown in FIG. 15. In many examples, the medial side of the stem will more closely match the SOMA data along a length of the implant compared to the lateral side. In some examples, a portion of the lateral side inclusive of a proximal lateral relief is shaped such that when the implant is positioned in the femur, there is minimal engagement between the proximal lateral relief and cortical bone on the lateral side. This aspect of the design improves ease of implantation by providing additional clearance while also not being relied upon to obtain stability which is achieved through engagement by other areas of the implant surface.

When medial-lateral dimensions in the engagement region 252 are calculated and otherwise established, an anterior-posterior dimension in engagement region 252 is determined. For this part of the design, the medial-lateral dimension is used as a guide in that a ratio of the medial-lateral dimension to the anterior-posterior dimension will be approximately 2.0, though an exact ratio depends on the location on the implant stem and the overall size of the implant. Additionally, the ratio may also become smaller in more distal locations in the engagement region. This ratio represents a general shape of the hip implant profile where the implant engages cortical bone on medial and lateral sides, but has minimal or no cortical bone engagement on the anterior and posterior sides. In this manner, anterior and posterior surfaces of the implant are expected to have limited cortical bone engagement or engage with cancellous bone only. SOMA data is once again analyzed to identify anterior-most and posterior-most bone locations at each transverse plane 280A-280G in engagement region 252, and an anterior-posterior dimension of implant 200 is sized to minimize cortical bone engagement in the anterior-posterior direction. The clearance between the cortical bone and anterior/posterior implant surfaces is shown in the view of implant 200 disposed in femur 310 in FIGS. 15 and 18.

In some examples, a size in the anterior-posterior direction may be further guided by characteristics of the SOMA data such as data that show that a dimension of the femur in the anterior direction is larger than a dimension in the posterior direction, these dimensions being orthogonal to the medial-lateral direction. This difference on the anterior and posterior sides may be used to adjust the anterior-posterior dimension to ensure that an expected fit in the anterior-posterior direction does not result in engagement with cortical bone, thereby avoiding a diminished effectiveness of the engagement on the medial and lateral sides. Controlling for this desired engagement in consideration of the medial-lateral and anterior-posterior directions results in an ML:AP ratio close to 2.0 in the engagement region. In some examples, there may be some cortical bone contact on either the anterior or posterior surface, but ultimately, such contact is minimized such that medial-lateral cortical fixation is established and preserved in any implantation scenario.

For the smallest implants used for the smallest group of femurs, an ML:AP ratio (medial-lateral dimension to anterior-posterior dimension) at medial resection point 219 may be in a range from 1.7 and 1.9. For the largest implants used for the largest group of femurs, the ML:AP ratio at medial resection point 219 may be in a range from 2.1 to 2.3.

Figure 18:
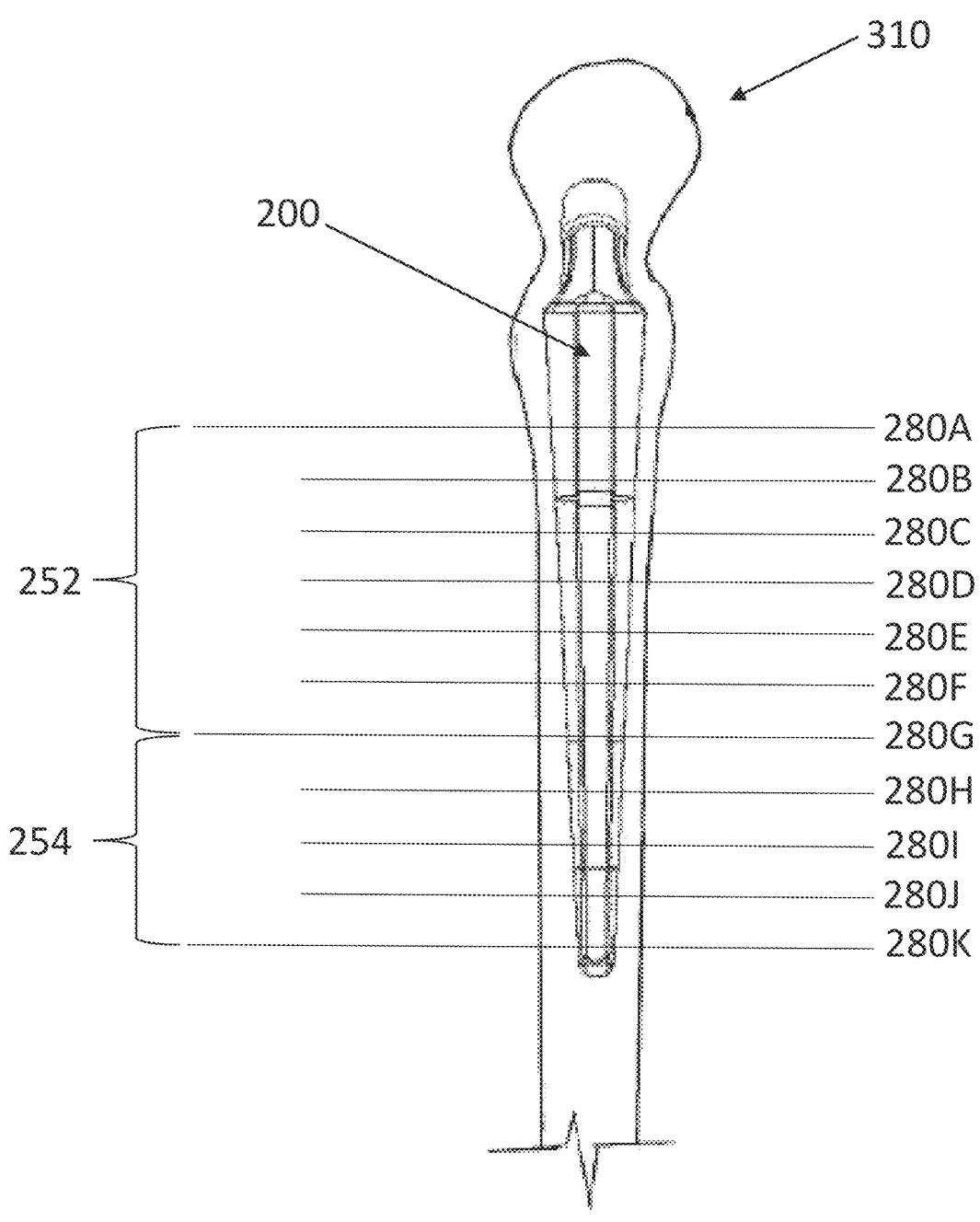

Turning to the design of clearance region 254, data points on the series of transverse planes, here planes 280H-280K, are retrieved based on the analysis of SOMA data. These are used to compare inner cortical surfaces of the bone between the medial and lateral sides. Here, clearance from the cortical bone is desired, so the medial-lateral dimension of the implant is sized to be clear of the cortical bone in its planned position disposed in the femur. As shown in FIGS. 16, 17 and 18, this means that implant 200 is clear of cortical bone in all directions in areas below ingrowth coating limit 232, and thus below transverse plane 280G. Similarly, clearance from the cortical bone is also desired in the anterior-posterior dimension. Advantageously, the present design approach produces a hip implant that provides ample clearance around a perimeter of the implant in clearance region 254, and in this way prevents any difficulties obtaining engagement in the engagement region due to circumstances such as a distal hang-up due to unintended engagement with cortical bone toward the distal tip.

Due to the difference in shape between larger femurs and smaller femurs, the ML:AP ratio in clearance region 254 is larger for larger hip implants. For the smallest implants used for the smallest group of femurs, the ML:AP ratio at the transition between regions, e.g., ingrowth coating limit 232, may be in a range from 0.9 to 1.1. For the largest implants used for the largest group of femurs, the ML:AP ratio at the transition between regions may be in a range from 1.7 to 1.9. ML:AP ratios have also been established based on an analysis of collected anatomical data. Using the previously mentioned SOMA data based on the CT scans of femurs of over 1300 individuals, the ML:AP ratios for twelve different size ranges, or groups, were calculated. These are outlined in Table 2 below.

TABLE 2

| Implant Size | ML:AP Ratio at Medial Resection Point | ML:AP Ratio at Ingrowth Coating Limit |
|---|---|---|
| 0 (93 mm) | 1.8 | 1.0 |
| 1 (96 mm) | 1.8 | 1.1 |
| 2 (99 mm) | 1.9 | 1.2 |
| 3 (101 mm) | 1.9 | 1.2 |
| 4 (103 mm) | 1.9 | 1.3 |
| 5 (105 mm) | 1.9 | 1.4 |
| 6 (107 mm) | 2.0 | 1.5 |
| 7 (109 mm) | 2.0 | 1.5 |
| 8 (111 mm) | 2.1 | 1.6 |
| 9 (113 mm) | 2.1 | 1.7 |
| 10 (115 mm) | 2.1 | 1.8 |
| 11 (117 mm) | 2.2 | 1.8 |

In conjunction with the above design process that establishes a profile of the hip implant along its length, angulation of anterior surfaces 212A, 222A and posterior surfaces 212B, 222B is determined. Proximal anterior and posterior surfaces 212A, 212B are angulated at proximal angle $\theta_1$ relative to one another while distal anterior and posterior surfaces 222A, 222B are angled at distal angle $\theta_2$ relative to one another. These surfaces and angles are shown in FIGS. 8 and 9, for example. In embodiments that employ the implant design method, the proximal angle $\theta_1$ of the implant is greater than distal angle $\theta_2$. The proximal and distal surfaces are separated at a transition depth 230, which corresponds to the apex where lateral surfaces 214B, 224B meet and lies entirely within engagement region 252 as shown in FIGS. 7A, 8 and 9, though may be close to or on ingrowth coating limit 232 in other embodiments. Angulations for these surfaces are established by analysis of data in the SOMA database to produce implants with ML:AP ratios that provide targeted engagement to either cortical or cancellous bone in engagement region 252 and clearance from cortical bone in clearance region 254 when hip implant is in an implanted position in a patient femur. Some exemplary locations of the transition depth on a length of the implant and specific anterior and posterior surface angles are summarized elsewhere in the disclosure and for the sake of brevity are not repeated here.

The transition depth 230, i.e., the transition location between proximal AP surfaces and distal AP surfaces, relative to medial resection point 219, was determined for twelve implant sizes based on data inclusive of elbow locations on lateral surfaces of hip implants in previously developed designs, such as Stryker® Accolade® II. Additionally, the previously referenced study of certain SOMA data was further processed to calculate proximal angle $\theta_1$ and distal angle $\theta_2$ for the same twelve implant sizes. These values are shown in Tables 3 and 4 below. It should be appreciated that in an alternative approach, the transition depth may also be determined using SOMA data aggregated and optionally sorted based on planned implant sizes.

TABLE 3

| Implant Size | Transition Distance from Medial Resection Point (mm) | % Length of Stem from Medial Resection Point |
|---|---|---|
| 0 (93 mm) | 9.3 | 10.0 |
| 1 (96 mm) | 9.7 | 10.1 |
| 2 (99 mm) | 10.0 | 10.1 |
| 3 (101 mm) | 10.4 | 10.3 |
| 4 (103 mm) | 10.7 | 10.4 |
| 5 (105 mm) | 10.5 | 10.0 |
| 6 (107 mm) | 10.4 | 9.7 |
| 7 (109 mm) | 10.2 | 9.4 |
| 8 (111 mm) | 10.0 | 9.0 |
| 9 (113 mm) | 9.9 | 8.8 |
| 10 (115 mm) | 9.7 | 8.4 |
| 11 (117 mm) | 9.6 | 8.2 |

TABLE 4

| Implant Size | Proximal Angle, $\theta_1$ (°) | Distal Angle, $\theta_2$ (°) | Difference (°) |
|---|---|---|---|
| 0 (93 mm) | 6.6 | 4.5 | 2.1 |
| 1 (96 mm) | 6.6 | 4.6 | 2.0 |
| 2 (99 mm) | 6.6 | 4.5 | 2.1 |
| 3 (101 mm) | 6.5 | 4.8 | 1.7 |
| 4 (103 mm) | 6.5 | 4.9 | 1.6 |
| 5 (105 mm) | 6.5 | 5.1 | 1.4 |
| 6 (107 mm) | 6.6 | 5.3 | 1.3 |

TABLE 4-continued

| Implant Size | Proximal Angle, $\theta_1$ (°) | Distal Angle, $\theta_2$ (°) | Difference (°) |
|---|---|---|---|
| 7 (109 mm) | 6.7 | 5.5 | 1.2 |
| 8 (111 mm) | 6.8 | 5.7 | 1.1 |
| 9 (113 mm) | 6.8 | 6.0 | 0.8 |
| 10 (115 mm) | 6.9 | 6.3 | 0.6 |
| 11 (117 mm) | 7.0 | 6.6 | 0.4 |

Figure 19:
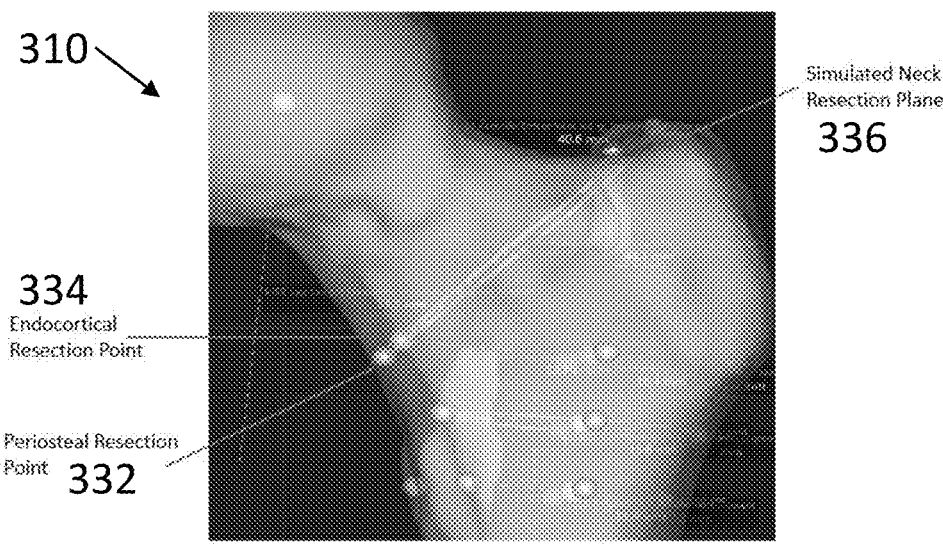
FIGS. 19-20 illustrate a step in a method of designing a hip implant according to some embodiments of the present disclosure.
Figure 20:
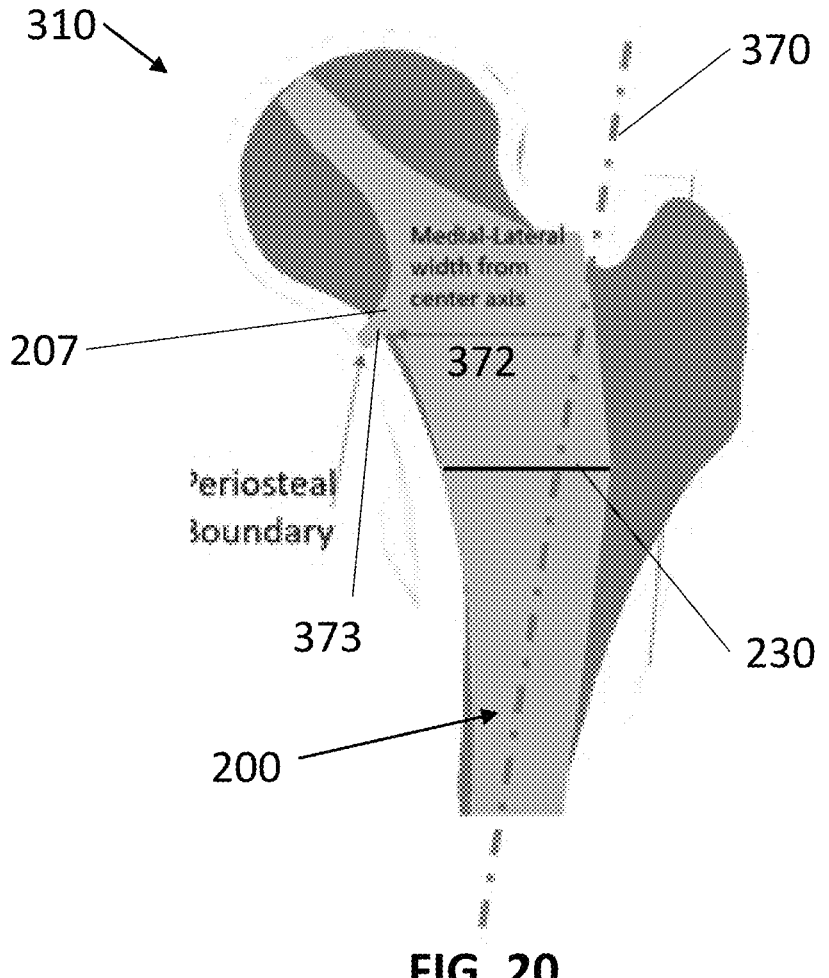

With continued reference to the described embodiment of the method of designing a hip implant, the completion of the design of the body, or stem, allows for the optional design of the collar. To design the collar, first, the implant body is overlaid on the representative femur 310 for the size range or other group of data points that the implant is designed for. As described elsewhere in the disclosure, such femur representation, and a position of the implant in the femur based on femoral head center and offset, may be established based on an analysis of SOMA data. This is shown, for example, in FIG. 20. To position the hip implant, a neck resection may be simulated for use in aligning the resection with interface 202. The neck resection may be represented by a neck resection plane 336 that extends across the femur from a periosteal resection point 332 on a medial side of the representative femur 310, as shown in FIG. 19. With implant 200 in an expected final implanted position within femur 310 as shown in FIG. 20, a distance 372 between femoral central axis 370, previously established through analysis of SOMA data, and medial resection point 219 of the implant stem, is determined. Then, a remaining distance between the medial resection point 219 and a periosteal boundary outside of an outer cortical bone surface may be used to define a medial-lateral collar dimension 373. In some specific examples, the medial-lateral collar dimension may be in a range from 5 mm to 7 mm. In other examples, the dimension 373 may be shorter or longer relative to the outer cortical bone surface, but in all cases, may be controlled and customized through the described method in a manner improved over previous approaches. In one exemplary variation, medial-lateral collar dimension 373 is sized so that in the implanted position, the collar does not overhang an outer surface of the cortical bone. In other embodiments, the collar design method may be performed as a standalone method.

In another embodiment, the method of designing a hip implant is employed to design implant 200' shown in FIGS. 21-22. Here, the steps of determining dimensions in the medial-lateral direction and the anterior-posterior direction, and the ratio of same, are determined in the same manner as that described for implant 200 and shown in FIGS. 14-18. As to a slope of the anterior and posterior surfaces of the implant, here, a transition depth 230' that is aligned with the ingrowth coating limit 232' is used to determine a proximal angle $\theta_1'$ and a distal angle $\theta_2'$, but the implant is otherwise designed in the same manner as described for implant 200.

Figure 23:
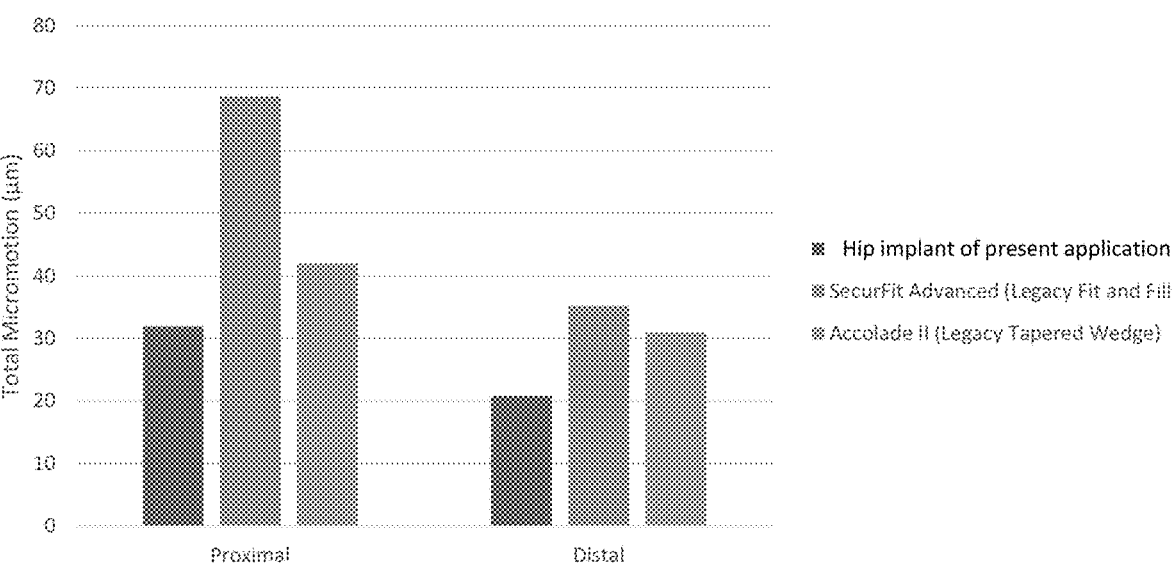
FIG. 23 is a chart including performance data of embodiments of the hip implant described in the present disclosure.

Design of a hip implant in the manner described in the present disclosure yields improved post-surgical performance relative to existing technologies. For instance, hip implants manufactured according to the designs of the present disclosure exhibited significantly lower micromotion in both the proximal and distal regions of the implant during stair-climb loading tests, as summarized in FIG. 23. The micromotion analysis involved an evaluation of micromotion in the stem of the implant relative to the femur at proximal and distal points on the stem.

In another aspect, the present disclosure relates to methods of manufacturing a hip broach or a hip implant. In some embodiments, at least one of a broach and an implant may be additively manufactured via a layer-by-layer 3D printing process. Examples of additive manufacturing methods that may be used include Shape Deposition Manufacturing ("SDM"), Selective Laser Power Processing ("SLPP"), Direct Metal Laser Sintering ("DMLS"), Selective Laser Sintering ("SLS"), Selective Laser Melting ("SLM"), Selective Heat Sintering ("SHS"), Electron Beam Melting ("EBM"), material jetting, binder jetting, or the like. Some of these techniques are disclosed in U.S. Pat. Nos. 7,537,664; 8,728,387; 9,180,010; and 9,456,901, the disclosures of which are hereby incorporated by reference herein in their entireties. In other embodiments, at least one of a broach and implant is injection molded. For example, material for the broach or implant may be melted under high heat and disposed in a mold to form the structure. One example of an injection molding process that may be utilized is disclosed in U.S. Pat. App. Pub. No. 2021/0237149, the disclosure of which is hereby incorporated by reference herein in its entirety.

In another aspect, the present disclosure relates to one or more steps in a method of placing a hip implant in a femur. In one embodiment, the method commences with pre-operative planning, neck resection, and preparation of the femoral canal already complete. Optionally, the aforementioned steps may be included as part of the method. In a first step, broaching is performed. When multiple broach sizes are available for performance of the broaching, the smallest one is inserted into the femoral canal first. This may be done by positioning the broach laterally and posteriorly relative to the femur bone. During the broaching action, and for illustration, with reference to broach 100 of FIG. 1, extraction teeth 120A, 120B remove cortical bone, compaction teeth 110A, 110B prepare and compact cancellous bone to receive the hip implant, and the distal diamond teeth 130 remove cortical and cancellous bone more aggressively than the extraction teeth. When broaching with the smallest size broach is complete, another broach of an incrementally larger size is retrieved and used to perform further broaching. This process of using broaches of incrementally larger sizes is repeated until a proper fit within the canal is achieved. Indications of proper fit during the broaching process include increased resistance to forward advancement, changing pitch of sound that results from mallet impacts to a broach handle, and/or lack of further motion or advancement of broach and rotational stability, which may be ascertained using the broach handle when secured to the broach.

Upon completion of broaching, trial reduction may optionally be performed by assembling an appropriate neck trial onto the broach and a head trial onto the neck trial and verifying the broach size. Whether or not trial reduction is performed, the final confirmed broach size is noted for hip implant selection as the broach size is expected to correspond to the correct implant size. The method continues with a step of ensuring that a bone surface surrounding the broach and the open end of the femoral canal is planar. In one example, this can be accomplished with a calcar planer that engages to a trunnion or other feature on the broach. In other examples, other tools may be used. When the surface is prepared, the broach may then be removed in preparation for placement of the hip implant.

A femoral hip implant with a size matching the final broach is retrieved for placement in the femur of the patient. As an optional step, the implant may be initially inserted into the femoral canal by hand until it meets resistance to position and orient the implant prior to using tools for implant securement. An implant inserter is then selected and attached to the implant for impaction of the implant into a secure position in the femoral canal. Firm seating of the implant is typically obtained either when the collar of the implant is just above or rests on the calcar bone or when resistance upon impaction suggests it is firmly seated. When implanted, and as discussed elsewhere in the disclosure, medial and lateral sides of the implant provide the primary engagement to cortical bone of the femur, with anterior and posterior surfaces being at least partially free from such engagement. Further, a distalmost part of the hip implant will be clear of cortical bone when the implant is firmly seated in its final position. The hip implant is implanted in the femoral canal in a cementless fashion.

Optional to this embodiment, a femoral head size may be chosen for the implant and verified. The head may then be secured to the implant and any desired verification of alignment and kinematics of the joint may be checked prior to finalization of the procedure.

In some embodiments, the method may be limited to steps involving the use of a broach alone, as described above. In other embodiments, the method may commence with a femoral canal ready to receive a hip implant and involve placement of the hip implant alone, as described above. In some embodiments, the broaching step of the method may involve the selection of an expected final broach size for a first broaching action, without the use of incrementally larger broaches to complete the broaching. In still further embodiments, the method of hip implant placement may be performed with the aid of robotics for one or more of the method steps. For instance, broach selection and broach use may be performed with a robotic arm controlled by software that includes all relevant surgical planning information. Similarly, hip implant placement may also be performed using robotics.

Although the invention herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A broach for use in a mammalian femur, the broach comprising:
a body with a proximal portion and a distal portion extending from the proximal portion, the proximal portion having a first surface with a plurality of first teeth and the distal portion having a second surface with a plurality of second teeth, at least one tooth of the plurality of second teeth being different from at least one tooth of the plurality of first teeth,
wherein the plurality of first teeth extend outward from the first surface so as to define a first plurality of linear troughs, each trough of the first plurality of linear troughs including a portion that extends unbroken across an entire side of the first surface,
wherein each one of the plurality of linear troughs is parallel to the others,
wherein at least one tooth of the plurality of second teeth includes a pointed protrusion extending outward from the second surface, and wherein the plurality of second teeth defines a second plurality of linear troughs and a third plurality of linear troughs on the second surface of the distal portion, the second plurality of linear troughs being transverse to the first plurality of linear troughs and the third plurality of linear troughs being transverse to the first and second plurality of linear troughs.

2. The broach of claim 1, wherein the pointed protrusions of the at least one tooth of the plurality of second teeth has leading surfaces oriented at a steeper angle than a flank trailing the pointed protrusion.

3. The broach of claim 2, wherein the plurality of second teeth extend around an entire perimeter of the distal portion.

4. The broach of claim 1, wherein each of the plurality of first teeth include an elongate sharp ridge surrounded on all sides by troughs separating each elongate sharp ridge.

5. The broach of claim 4, wherein the proximal portion further comprises a third surface with a plurality of third teeth different from the plurality of first teeth, the third surface not overlapping the first surface and each of the first surface and the third surface extending along a length of the proximal portion.

6. The broach of claim 4, wherein the proximal portion further comprises a third surface with a plurality of third teeth, at least one tooth of the plurality of third teeth having an elongate flat protruding ridge.

7. The broach of claim 6, wherein the body includes a medial surface, a lateral surface, an anterior surface and a posterior surface, the first surface of the proximal portion including the medial and lateral surfaces and the third surface of the proximal portion including the anterior and posterior surfaces.

8. The broach of claim 1, wherein at least some of the plurality of second teeth are located less than 25% of a distance from a distal tip of the body to a proximal end of the body.

9. The broach of claim 8, wherein the distal portion is located entirely within 40% of a distance from the distal tip of the body to the proximal end of the body.

10. The broach of claim 9, wherein the plurality of second teeth extend over a majority of the second surface and the second surface is coincident with the distal portion.

11. The broach of claim 10, wherein the plurality of second teeth are only in the distal portion.

12. The broach of claim 1, wherein the proximal portion includes a medial proximal end and a transition between the proximal portion and the distal portion is in a range of 60 mm to 80 mm from the medial proximal end.

13. A broach for use in a mammalian femur, the broach comprising:
a body with a proximal portion and a distal portion separated from the proximal portion by a transition region, the proximal portion having a first toothed surface extending over a first distance along a length of the body and the distal portion having a second toothed surface extending over a second distance along the length of the body,
wherein the first distance is greater than the second distance,
wherein the first toothed surface has a plurality of first cutting surfaces and the second toothed surface has a plurality of second cutting surfaces,
wherein a first protruding end of at least one first cutting surface of the plurality of first cutting surfaces is longer than a second protruding end of at least one second cutting surface of the plurality of second cutting surfaces, wherein the plurality of first cutting surfaces defines a first plurality of linear troughs on the first toothed surface of the proximal portion, each one of the plurality of linear troughs being parallel to the others, and wherein the plurality of second cutting surfaces defines a second plurality of linear troughs and a third plurality of linear troughs on the second toothed surface of the distal portion, the second plurality of linear troughs being transverse to the first plurality of linear troughs and the third plurality of linear troughs being transverse to the first and second plurality of linear troughs.

14. The broach of claim 13, wherein the first protruding end of the at least one cutting surface of the plurality of first cutting surfaces is an elongate ridge and the second protruding end of the at least one cutting surface of the plurality of second cutting surfaces is a sharp point.

15. The broach of claim 13, wherein the first distance is in a range from 50% to 70% of a combined first and second distance.

16. The broach of claim 13, wherein when the broach is fully disposed in a femoral canal of the mammalian femur, the transition region is aligned with a location on the femur where a medial to lateral width of the femur changes by an amount in a range of 0.25 mm per 10 mm length to 0.35 mm per 10 mm length.

17. The broach of claim 13, wherein when the broach is fully disposed in a femoral canal of the mammalian femur, the transition region is aligned with a location on the femur where a first dimension from an anterior limit of the femur to a posterior limit of the femur is between 1.0 and 1.2 times a second dimension from a medial limit of the femur to lateral limit of the femur.

18. A broach for use in preparing a femur to receive an implant, the broach comprising:

a proximal portion extending along a first portion of a length of the broach; and a distal portion extending along a second portion of the length of the broach, the distal portion abutting the proximal portion, wherein when the broach is advanced into a femur, a distal tip of the distal portion is a leading end of the broach and a proximal end of the proximal portion is a trailing end of the broach, wherein the proximal portion includes a plurality of first cutting surfaces, the plurality of first cutting surfaces defining a first plurality of linear troughs on a surface of the proximal portion, each one of the plurality of linear troughs being parallel to the others, and wherein the distal portion includes a plurality of second cutting surfaces, the plurality of second cutting surfaces defining a second plurality of linear troughs and a third plurality of linear troughs on a surface of the distal portion, the second plurality of linear troughs being transverse to the first plurality of linear troughs and the third plurality of linear troughs being transverse to the first and second plurality of linear troughs.

19. The broach of claim 18, wherein each of the second cutting surfaces of the plurality of second cutting surfaces include pointed tips.

20. The broach of claim 18, wherein the proximal portion further comprises a plurality of third cutting surfaces different from the plurality of first cutting surfaces and the plurality of second cutting surfaces.

* * * * *